US012678092B2

(12) United States Patent
Kong et al.

(10) Patent No.: US 12,678,092 B2
(45) Date of Patent: Jul. 14, 2026

(54) SYSTEMS AND METHODS FOR ASSESSING MEDICAL CONDITIONS SUCH AS INFLAMMATION, AUTOIMMUNITY, AND AUTISM SPECTRUM DISORDER (ASD), AND TREATMENTS THEREOF

(71) Applicant: The General Hospital Corporation, Boston, MA (US)

(72) Inventors: Xue-Jun Kong, Lexington, MA (US); Kenneth Kwong, Boston, MA (US); Suk-Tak Chan, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 220 days.

(21) Appl. No.: 18/697,263

(22) PCT Filed: Sep. 30, 2022

(86) PCT No.: PCT/US2022/077347
§ 371 (c)(1),
(2) Date: Mar. 29, 2024

(87) PCT Pub. No.: WO2023/056419
PCT Pub. Date: Apr. 6, 2023

(65) Prior Publication Data
US 2025/0281101 A1 Sep. 11, 2025

Related U.S. Application Data

(60) Provisional application No. 63/250,493, filed on Sep. 30, 2021.

(51) Int. Cl.
A61B 5/00 (2006.01)
A61B 5/145 (2006.01)
(Continued)

(52) U.S. Cl.
CPC ........ *A61B 5/4076* (2013.01); *A61B 5/14542* (2013.01); *A61B 5/14546* (2013.01);
(Continued)

(58) Field of Classification Search
CPC .............. A61B 5/4076; A61B 5/14542; A61B 5/14546; A61B 5/7246; A61B 5/7475;
(Continued)

(56) References Cited

U.S. PATENT DOCUMENTS

2004/0209311 A1* 10/2004 Latov ................. G01N 33/6854
435/7.1
2011/0171232 A1* 7/2011 Lin ........................ A61K 38/02
424/116
(Continued)

OTHER PUBLICATIONS

Abou-Donia, Mohamed B., et al. "De novo blood biomarkers in autism: autoantibodies against neuronal and glial proteins." Behavioral Sciences 9.5 (2019): 47.
(Continued)

*Primary Examiner* — Rex R Holmes
(74) *Attorney, Agent, or Firm* — QUARLES & BRADY LLP

(57) ABSTRACT

A system for evaluating a subject, including: a processor in communication with a carbon monoxide (CO) detector, and a memory in communication with the processor having stored thereon a set of instructions which, when executed by the processor, cause the processor to: receive, from the CO detector, a measure of CO in a subject suspected of having at least one of autism spectrum disorder (ASD), autoimmunity, or inflammation; obtain a level of at least one biomarker associated with the subject based on receiving the measure of CO in the subject; and generate a report based on obtaining the level of the at least one biomarker.

22 Claims, 18 Drawing Sheets

(51) Int. Cl.
    *G16H 15/00*        (2018.01)
    *G16H 20/10*        (2018.01)
(52) U.S. Cl.
    CPC .......... *A61B 5/7246* (2013.01); *A61B 5/7475*
                (2013.01); *G16H 15/00* (2018.01); *G16H*
                *20/10* (2018.01); *A61B 2560/0462* (2013.01)
(58) Field of Classification Search
    CPC . A61B 2560/0462; A61B 5/082; A61B 5/097;
                A61B 5/168; G16H 15/00; G16H 20/10;
                G01N 33/564; G01N 2800/30; G01N
                33/6893; G01N 33/6896; A61K 35/747;
                                                A61P 29/00
    See application file for complete search history.

(56)                References Cited

U.S. PATENT DOCUMENTS

2013/0216989  A1      8/2013   Cuthbert
2016/0339065  A1*    11/2016   Adams ...................... A61P 1/00
2017/0055573  A1*     3/2017   Utley ................... A61B 5/4266
2019/0050534  A1      2/2019   Apte et al.
2019/0079073  A1*     3/2019   Hyde ................. A61B 10/0051

OTHER PUBLICATIONS

Alam, Reza, Hamid M. Abdolmaleky, and Jin-Rong Zhou. "Microbiome, inflammation, epigenetic alterations, and mental diseases." American Journal of Medical Genetics Part B: Neuropsychiatric Genetics 174.6 (2017): 651-660.
Aman, Michael G., et al. "The aberrant behavior checklist: a behavior rating scale for the assessment of treatment effects." American journal of mental deficiency 89.5 (1985): 485-491.
Bashir, Shahid, and Laila Al-Ayadhi. "Endothelial antibody levels in the sera of children with autism spectrum disorders." Journal of the Chinese Medical Association 78.7 (2015): 414-417.
Bolte, Sven, Fritz Poustka, and John N. Constantino. "Assessing autistic traits: cross-cultural validation of the social responsiveness scale (SRS)." Autism Research 1.6 (2008): 354-363.
Braunschweig, Daniel, et al. "Autism-specific maternal autoantibodies recognize critical proteins in developing brain." Translational psychiatry 3.7 (2013): e277-e277.
Breuss, Martin W., et al. "Tubulins and brain development—The origins of functional specification." Molecular and Cellular Neuroscience 84 (2017): 58-67.
Busner, Joan, and Steven D. Targum. "The clinical global impressions scale: applying a research tool in clinical practice." Psychiatry (edgmont) 4.7 (2007): 28.
Cao, Xia, et al. "Dysbiotic gut microbiota and dysregulation of cytokine profile in children and teens with autism spectrum disorder." Frontiers in neuroscience 15 (2021): 635925.
Chain, Jennifer L., et al. "Autoantibody biomarkers for basal ganglia encephalitis in sydenham chorea and pediatric autoimmune neuropsychiatric disorder associated with streptococcal infections." Frontiers in psychiatry 11 (2020): 564.
Chao, Shiou-Huei, et al. "Diversity of lactic acid bacteria in suan-tsai and fu-tsai, traditional fermented mustard products of Taiwan." International Journal of Food Microbiology 135.3 (2009): 203-210.
Connery, Kathleen, et al. "Intravenous immunoglobulin for the treatment of autoimmune encephalopathy in children with autism." Translational psychiatry 8.1 (2018): 148.
Connolly, Anne M., et al. "Brain-derived neurotrophic factor and autoantibodies to neural antigens in sera of children with autistic spectrum disorders, Landau-Kleffner syndrome, and epilepsy." Biological psychiatry 59.4 (2006): 354-363.
Connolly, Anne M., et al. "Serum autoantibodies to brain in Landau-Kleffner variant, autism, and other neurologic disorders." The Journal of pediatrics 134.5 (1999): 607-613.

Cox, Carol J., et al. "Antineuronal antibodies in a heterogeneous group of youth and young adults with tics and obsessive-compulsive disorder." Journal of child and adolescent psychopharmacology 25.1 (2015): 76-85.
Dale, Russell C., et al. "Antibodies to surface dopamine-2 receptor in autoimmune movement and psychiatric disorders." Brain 135.11 (2012): 3453-3468.
DeSantis, Todd Z., et al. "Greengenes, a chimera-checked 16S rRNA gene database and workbench compatible with ARB." Applied and environmental microbiology 72.7 (2006): 5069-5072.
DiStasio, Marcello M., et al. "T lymphocytes and cytotoxic astrocyte blebs correlate across autism brains." Annals of neurology 86.6 (2019): 885-898.
Erdman, S. E., and T. Poutahidis. "Microbes and oxytocin: benefits for host physiology and behavior." International review of neurobiology 131 (2016): 91-126.
Esnafoglu, Erman, et al. "Evaluation of serum Neuron-specific enolase, S100B, myelin basic protein and glial fibrilliary acidic protein as brain specific proteins in children with autism spectrum disorder." International Journal of Developmental Neuroscience 61 (2017): 86-91.
Fattorusso, Antonella, et al. "Autism spectrum disorders and the gut microbiota." Nutrients 11.3 (2019): 521.
Gonzalez-Gronow, Mario, et al. "Catalytic autoantibodies against myelin basic protein (MBP) isolated from serum of autistic children impair in vitro models of synaptic plasticity in rat hippocampus." Journal of neuroimmunology 287 (2015): 1-8.
Guloksuz, Selin Aktan, et al. "Elevated plasma concentrations of S100 calcium-binding protein B and tumor necrosis factor alpha in children with autism spectrum disorders." Revista Brasileira de Psiquiatria 39.3 (2017): 195-200.
Kealy, John, Chris Greene, and Matthew Campbell. "Blood-brain barrier regulation in psychiatric disorders." Neuroscience letters 726 (2020): 133664.
Kern, Janet K., et al. "Relevance of neuroinflammation and encephalitis in autism." Frontiers in Cellular Neuroscience 9 (2016): 519.
Kirvan, Christine A., et al. "Antibody-mediated neuronal cell signaling in behavior and movement disorders." Journal of neuroimmunology 179.1-2 (2006): 173-179.
Kong, Xuejun, et al. "New and preliminary evidence on altered oral and gut microbiota in individuals with autism spectrum disorder (ASD): implications for ASD diagnosis and subtyping based on microbial biomarkers." Nutrients 11.9 (2019): 2128.
Kong, Xue-Jun, et al. "Probiotics and oxytocin nasal spray as neuro-social-behavioral interventions for patients with autism spectrum disorders: a pilot randomized controlled trial protocol." Pilot and Feasibility Studies 6 (2020): 1-9.
Kong, Xue-Jun, et al. "Probiotic and oxytocin combination therapy in patients with autism spectrum disorder: a randomized, double-blinded, placebo-controlled pilot trial." Nutrients 13.5 (2021): 1552.
Kwong, Kenneth K., and Suk-tak Chan. "The role of carbon monoxide and heme oxygenase-1 in COVID-19." Toxicology Reports 7 (2020): 1170.
Lewis, Simon J., and Kenneth W. Heaton. "Stool form scale as a useful guide to intestinal transit time." Scandinavian journal of gastroenterology 32.9 (1997): 920-924.
Liao, Po-Lin, et al. "Toxicity studies of Lactobacillus plantarum PS128TM isolated from spontaneously fermented mustard greens." Foods 8.12 (2019): 668.
Light, A., et al. "Carboxyhemoglobin levels in smokers vs. non-smokers in a smoking environment." Respir Care 52.11 (2007): 1576.
Liu, Hu, et al. "Butyrate: a double-edged sword for health?." Advances in nutrition 9.1 (2018): 21-29.
Liu, Yen-Wenn, et al. "Effects of Lactobacillus plantarum PS128 on children with autism spectrum disorder in Taiwan: a randomized, double-blind, placebo-controlled trial." Nutrients 11.4 (2019): 820.
Liu, Wei-Hsien, et al. "Alteration of behavior and monoamine levels attributable to Lactobacillus plantarum PS128 in germ-free mice." Behavioural brain research 298 (2016): 202-209.
Liu, Wei-Hsien, et al. "Genome architecture of Lactobacillus plantarum PS128, a probiotic strain with potential immunomodulatory activity." Gut Pathogens 7 (2015): 1-7.

(56)                    References Cited

OTHER PUBLICATIONS

Maenner, Matthew J. "Prevalence of autism spectrum disorder among children aged 8 years—autism and developmental disabilities monitoring network, 11 sites, United States, 2016." MMWR. Surveillance Summaries 69 (2020).

Masi, A., et al. "Cytokine aberrations in autism spectrum disorder: a systematic review and meta-analysis." Molecular psychiatry 20.4 (2015): 440-446.

Matsuura, Takanori, et al. "Relationship between oxytocin and pain modulation and inflammation." Journal of UOEH 38.4 (2016): 325-334.

McIver, Lauren J., et al. "bioBakery: a meta'omic analysis environment." Bioinformatics 34.7 (2018): 1235-1237.

Melamed, Isaac R., et al. "A pilot study of high-dose intravenous immunoglobulin 5% for autism: Impact on autism spectrum and markers of neuroinflammation." Autism Research 11.3 (2018): 421-433.

Morita, Makiko, et al. "Dopamine D2L receptor is required for visual discrimination and reversal learning." Molecular Neuropsychiatry 2.3 (2016): 124-132.

Mostafa, Gehan Ahmed, and Laila Yousef Al-Ayadhi. "A lack of association between hyperserotonemia and the increased frequency of serum anti-myelin basic protein auto-antibodies in autistic children." Journal of neuroinflammation 8 (2011): 1-8.

Pavăl, Denis. "A dopamine hypothesis of autism spectrum disorder." Developmental neuroscience 39.5 (2017): 355-360.

Ryter, Stefan W. "Heme oxygenase-1/carbon monoxide as modulators of autophagy and inflammation." Archives of biochemistry and biophysics 678 (2019): 108186.

Ryter, Stefan W., and Augustine MK Choi. "Targeting heme oxygenase-1 and carbon monoxide for therapeutic modulation of inflammation." Translational Research 167.1 (2016): 7-34.

Sakurai, Yoshihiko. "Autoimmune aspects of Kawasaki disease." J Investig Allergol Clin Immunol 29.4 (2019): 251-261.

Schimmel, Jonathan, et al. "Carboxyhemoglobin levels induced by cigarette smoking outdoors in smokers." Journal of Medical Toxicology 14 (2018): 68-73.

Segata, Nicola, et al. "Metagenomic biomarker discovery and explanation." Genome biology 12 (2011): 1-18.

Shimasaki, Craig, et al. "Evaluation of the Cunningham Panel™ in pediatric autoimmune neuropsychiatric disorder associated with streptococcal infection (PANDAS) and pediatric acute-onset neuropsychiatric syndrome (PANS): Changes in antineuronal antibody titers parallel changes in patient symptoms." Journal of neuroimmunology 339 (2020): 577138.

Strati, Francesco, et al. "New evidences on the altered gut microbiota in autism spectrum disorders." Microbiome 5 (2017): 1-11.

Wagener, Frank ADTG, et al. "Targeting the heme-heme oxygenase system to prevent severe complications following COVID-19 infections." Antioxidants 9.6 (2020): 540.

Weisman, Omri, and Ruth Feldman. "Oxytocin administration affects the production of multiple hormones." Psychoneuroendocrinology 38.5 (2013): 626-627.

Yang, Xiaolei, et al. "Sialic acid and anti-ganglioside antibody levels in children with autism spectrum disorders." Brain research 1678 (2018): 273-277.

Zou, Tianle, et al. "Autoantibody and autism spectrum disorder: A systematic review." Research in Autism Spectrum Disorders 75 (2020): 101568.

* cited by examiner

CaM Kinase II — 94.4%

Anti–Tubulin — 94.4%

Endothelial Cell IgG/IgM — 82.6%

Anti–Dopamine Receptor D1 — 77.8%

SpCO — 64.7%

S100B — 64%

Anti–Lysoganglioside GM1 — 27.8%

Anti–Dopamine Receptor D2L — 27.8%

IL–1b — 24%

MBP — 16%

Proportion of Positive Measurements (%)

0%    25%    50%    75%

(a)

(b)

(a)

(b)

1000

RECEIVE A MEASURE OF CO IN A SUBJECT SUSPECTED OF HAVING AT LEAST ONE OF AUTISM SPECTRUM DISORDER (ASD), AUTOIMMUNITY, OR INFLAMMATION — 1002

OBTAIN A LEVEL OF AT LEAST ONE BIOMARKER ASSOCIATED WITH THE SUBJECT BASED ON RECEIVING THE MEASURE OF CO IN THE SUBJECT — 1004

GENERATE A REPORT BASED ON OBTAINING THE LEVEL OF THE AT LEAST ONE BIOMARKER — 1006

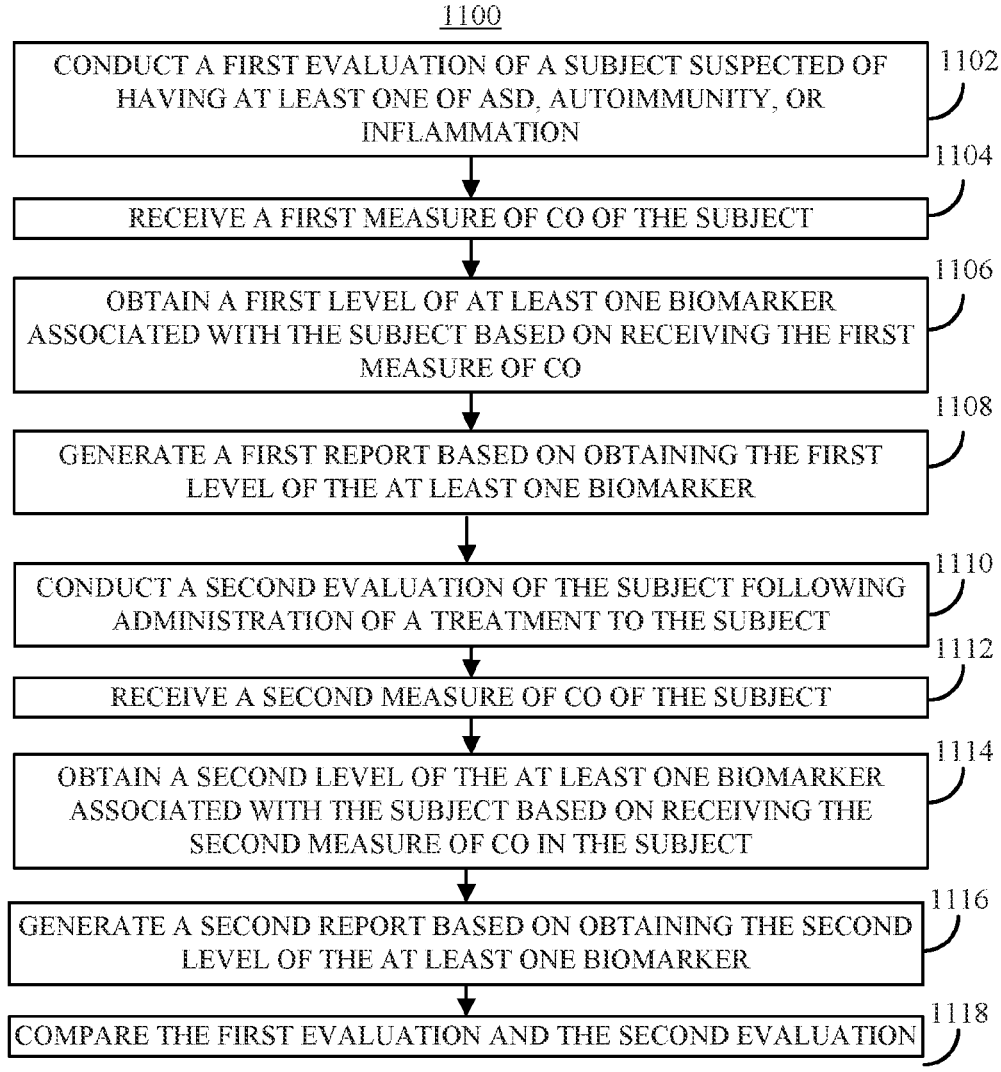

1100

CONDUCT A FIRST EVALUATION OF A SUBJECT SUSPECTED OF HAVING AT LEAST ONE OF ASD, AUTOIMMUNITY, OR INFLAMMATION — 1102

RECEIVE A FIRST MEASURE OF CO OF THE SUBJECT — 1104

OBTAIN A FIRST LEVEL OF AT LEAST ONE BIOMARKER ASSOCIATED WITH THE SUBJECT BASED ON RECEIVING THE FIRST MEASURE OF CO — 1106

GENERATE A FIRST REPORT BASED ON OBTAINING THE FIRST LEVEL OF THE AT LEAST ONE BIOMARKER — 1108

CONDUCT A SECOND EVALUATION OF THE SUBJECT FOLLOWING ADMINISTRATION OF A TREATMENT TO THE SUBJECT — 1110

RECEIVE A SECOND MEASURE OF CO OF THE SUBJECT — 1112

OBTAIN A SECOND LEVEL OF THE AT LEAST ONE BIOMARKER ASSOCIATED WITH THE SUBJECT BASED ON RECEIVING THE SECOND MEASURE OF CO IN THE SUBJECT — 1114

GENERATE A SECOND REPORT BASED ON OBTAINING THE SECOND LEVEL OF THE AT LEAST ONE BIOMARKER — 1116

COMPARE THE FIRST EVALUATION AND THE SECOND EVALUATION — 1118

FIG. 11

SYSTEMS AND METHODS FOR ASSESSING MEDICAL CONDITIONS SUCH AS INFLAMMATION, AUTOIMMUNITY, AND AUTISM SPECTRUM DISORDER (ASD), AND TREATMENTS THEREOF

CROSS-REFERENCE TO RELATED APPLICATIONS

The present application is the U.S. National Stage Entry of PCT/US2022/077347, filed Sep. 30, 2022, which claims priority to U.S. Provisional Patent Application No. 63/250,493 that was filed Sep. 30, 2021, the entire contents of each of which are hereby incorporated by reference for all purposes.

BACKGROUND OF THE INVENTION

Autism Spectrum Disorder (ASD) is an intricate neurodevelopmental disorder featuring social deficit and repetitive restrictive behaviors. According to the latest Centers for Disease Control and Prevention (CDC) release, the prevalence of ASD has rapidly increased to 1 in 54 children in the USA. Inflammatory mechanism, autoimmunity, and gut-brain axis have been implicated in the etiology and pathogenesis of ASD. Anti-inflammatory agents, conventional immunotherapy and probiotics have shown promising therapeutic effects to modify the core symptoms of ASD. Inflammatory mechanisms were widely reported to be linked with ASD and its severity. Previous studies found that inflammatory cytokines were significantly elevated in ASD subjects when compared with healthy controls. Meantime the brain injury and inflammatory markers, glial fibrillary acidic protein (GFAP), myelin basic protein (MBP), and S100 calcium-binding protein B (S100B), were also found to be more enriched in ASD children than healthy controls. Meantime these brain injury markers and cytokine release trigger glial cell activation and inflammatory process in the brain. There is motivation to further understand and clinically apply the concept of inflammation, autoimmunity, and gut-brain axis in the ASD population.

BRIEF SUMMARY OF THE INVENTION

In one embodiment, a system for evaluating a subject, including: a processor in communication with a carbon monoxide (CO) detector, and a memory in communication with the processor having stored thereon a set of instructions which, when executed by the processor, cause the processor to: receive, from the CO detector, a measure of CO in a subject suspected of having at least one of autism spectrum disorder (ASD), autoimmunity, or inflammation; obtain a level of at least one biomarker associated with the subject based on receiving the measure of CO in the subject; and generate a report based on obtaining the level of the at least one biomarker.

In another embodiment, a method for evaluating a subject, including: receiving, from a CO detector in communication with a carbon monoxide (CO) detector, a measure of CO in a subject suspected of having at least one of autism spectrum disorder (ASD), autoimmunity, or inflammation; obtaining, by the processor, a level of at least one biomarker associated with the subject based on receiving the measure of CO in the subject; and generating, by the processor, a report based on obtaining the level of the at least one biomarker.

In still another embodiment, a system for assessing efficacy of treatment of a subject suspected of having at least one of Autism Spectrum Disorder (ASD), autoimmunity, or inflammation, including: a processor in communication with a carbon monoxide (CO) detector, and a memory in communication with the processor having stored thereon a set of instructions which, when executed by the processor, cause the processor to: conduct a first evaluation of a subject suspected of having at least one of ASD, autoimmunity, or inflammation, including: receiving, from the carbon monoxide (CO) detector, a first measure of CO of the subject, obtaining a first level of at least one biomarker associated with the subject based on receiving the first measure of CO, generating a first report based on obtaining the first level of the at least one biomarker; conduct a second evaluation of the subject following administration of a treatment to the subject, including: receiving, from the CO detector, a second measure of CO of the subject, obtaining a second level of the at least one biomarker associated with the subject based on receiving the second measure of CO in the subject, and generating a second report based on obtaining the second level of the at least one biomarker; and compare the first evaluation and the second evaluation.

In yet another embodiment, a method of assessing efficacy of treatment of a subject suspected of having at least one of Autism Spectrum Disorder (ASD), autoimmunity, or inflammation, including: conducting a first evaluation of a subject suspected of having at least one of ASD, autoimmunity, or inflammation, including: receiving, by a processor in communication with a carbon monoxide (CO) detector, a first measure of CO of the subject, obtaining, by the processor, a first level of at least one biomarker associated with the subject based on receiving the first measure of CO, generating, by the processor, a first report based on obtaining the first level of the at least one biomarker; conducting a second evaluation of the subject following administration of a treatment to the subject, including: receiving, by the processor from the CO detector, a second measure of CO of the subject, obtaining, by the processor, a second level of the at least one biomarker associated with the subject based on receiving the second measure of CO in the subject, and generating, by the processor, a second report based on obtaining the second level of the at least one biomarker; and comparing, by the processor, the first evaluation and the second evaluation.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

FIG. 11 shows an example of a process for assessing efficacy of treatment of a subject suspected of having at least one of Autism Spectrum Disorder (ASD), autoimmunity, or inflammation in accordance with some embodiments of the disclosed subject matter.

DETAILED DESCRIPTION OF THE INVENTION

Figure 1:
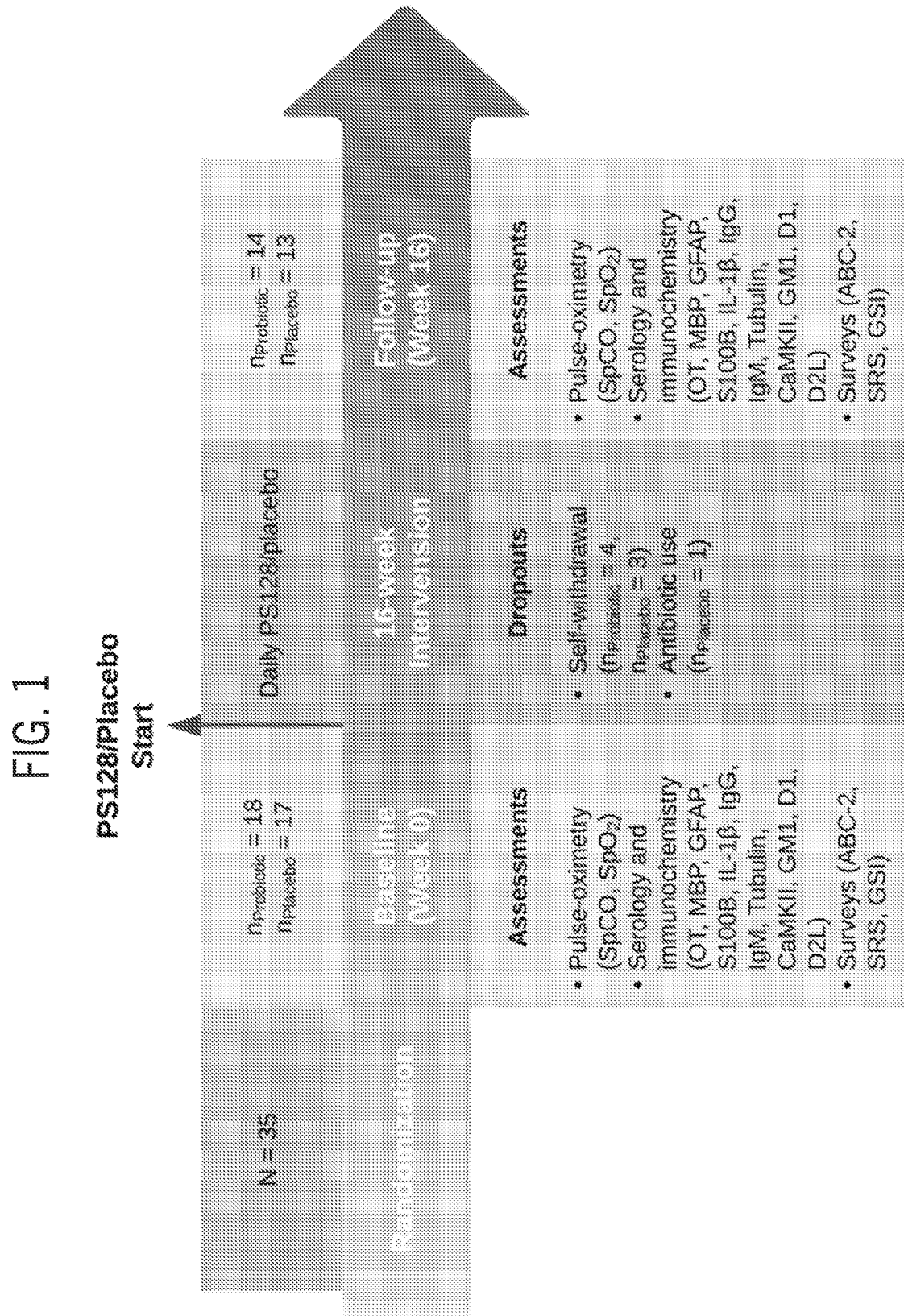
FIG. 1 shows a timeline of study design, subject dropouts, and assessed variables.

The present disclosure provides for assessing medical conditions such as inflammation, autoimmunity, and autism spectrum disorder (ASD) and treatments thereof.

The present disclosure includes a system for evaluating a subject including a processor with a memory, a carbon monoxide (CO) detector, and instructions for receiving a measure of CO in a subject, at least one biomarker associated with the subject based on the measure of CO in the subject, and a report.

In one aspect of the disclosed technology, a subject is a person experiencing autism spectrum disorder, inflammation, or autoimmunity. In one embodiment of a subject experiencing inflammation, the inflammation may be neuroinflammation, autoimmunity-mediated neuroinflammation, or systemic inflammation. Alternatively, the inflammation may be the result of infection with an infectious agent, such as SARS-COV-2, and development of Coronavirus Disease-2019 (COVID-19). In further aspects, inflammation may also be the result of allergy. In yet other aspects, the examples of neuroinflammation caused by autoimmunity include Pediatric Autoimmune Neuropsychiatric Disorders Associated with Streptococcal Infections (PANDAS), Hashimoto's encephalopathy, NMDAR antibody encephalitis, etc.

In one aspect of the disclosed technology, a carbon monoxide detector may be used to determine a measure of carbon monoxide. Several methods for CO detection are established in the art, including colorimetric, spectrophotometric, electrical, and electrochemical methods. In one embodiment, the CO detection method is spectrophotometric detection with at least one wavelength.

In one embodiment, the measure of CO is concentration. In some embodiments the measure of CO may be performed by measuring a proxy molecule having a known and proportional relationship to the concentration of CO. In one embodiment, the proxy molecule may be carboxyhemoglobin. In a related embodiment, the measure of CO may be a measure of carbon monoxide in blood (SpCO). The values of SpCO may range from 0-1%, 0-5%, 0-10%, 5-10%, 10-15%, 0-20%, 0-30%.

In another aspect the system for evaluating a subject, including the CO detector, may be coupled to the subject. In one embodiment the system and CO detector may be portable. In one embodiment the CO detector may be a wearable device. In one embodiment, the CO detector of the system is worn on a finger of the subject during the measurement. In other embodiments the CO detector is a CO-oximetry device or a pulse CO-oximetry device worn on the finger of a subject.

A biomarker is defined as a measurable metric in a subject whose presence is indicative of some phenomenon such as disease, infection, or environmental exposure. In another aspect of the disclosed technology, the level of at least one biomarker associated with the subject based on receiving the measure of CO in the subject may be obtained. In some embodiments the biomarkers include anti-tubulin, CaM kinase II, anti-dopamine receptor D1, or anti-lysoganglioside GM1, HO-1, autoantibodies including AECA and Cunningham Panel, inflammatory serum markers including cytokine interleukin-1$\beta$ (IL-1$\beta$), brain injury markers (S100B, GFAP, MBP), OT serum level, microbiome profile, GI symptom severity, ASD core symptom severity. In one preferred embodiment, the biomarker may be ganglioside-monosialic acid (GM1).

In one embodiment, the system or method may report the measure of CO in the subject and, by correlation, a measure or level of at least one biomarker in the subject. In another aspect, at least one biomarker may be correlated to the severity of symptoms experienced by the subject. In another aspect, the measure of CO in a subject is additionally correlated to the biomarker. These correlations may be represented by calibration curves, algorithms, artificial intelligence, or machine learning algorithms. The correlation of the measure of CO in a subject to the biomarker and the correlation of the biomarker to the severity of symptoms experienced by the subject may be leveraged in methods of using the system. In one embodiment, the report generated by the system may indicate a diagnosis, treatment, or subgroup of the subject. In some embodiments the report may indicate or predict that the evaluated subject belongs to one or more subgroups. For example, in certain cases, ASD has 3 subtypes based upon continuous scales of social communication (SC) and fixed interest and repetitive behaviors (FIRB). Subgroups of ASD may include group 1 where there is moderate SC impairment, and lowest FIRB scores, group 2 where there is low SC impairment, and moderate FIRB scores, or group 3 where there is high SC impairment, and high FIRB scores. In one embodiment the report generated by the system may indicate or predict a subgroup based upon the correlations of the measure of CO, at least one biomarker, and symptom severity. The report generated by the system may be displayed on a user interface. In some embodiment the user interface may be a graphical user interface, a command line interface, an icon, a menu, a graphic, a text-based user interface, a touch user interface, a human voice, a human-computer interaction, a window interface, a conversational user interface, a form-based user interface, a touchscreen, a task-focused interface, or an intelligent user interface. In some embodiments the report may be provided by paper, digital, auditory, or cloud-based reporting methods.

In another aspect, the measure of CO in a subject may be performed by collecting one or more measurements, such as a first time point and a second time point. In one embodiment the measure of CO in a subject is a mean average of one or more measures of CO. In one embodiment, the first time point and second time point are collected sequentially with a period of time separating them. The period of time separating the measurements may be from 0.0 minutes to 10 minutes, from 0.5 minutes to 5.0 minutes, from 1.0 minutes to 2.0 minutes, or from 1.0 minutes to 3.0 minutes or from 0.5 minutes to 10 minutes.

In another aspect, the system and methods disclosed herein may be used to evaluate treatment of the subject suspected of having ASD, inflammation, or autoimmunity. In one embodiment the treatment may include administering a probiotic to the subject. In some embodiments, treatment includes anti-inflammatory treatments, immunomodulatory and immunosuppressant treatments, intravenous immuno-globulin (IVIg), monoclonal antibodies, behavioral management therapy, cognitive behavioral therapy, selective serotonin re-uptake inhibitors, tricyclics, psychoactive or antipsychotic medications, stimulants, anti-anxiety medications, anticonvulsants, gluten-free diet, or casein-free diet, vagal nerve stimulation, transcranial magnetic treatment, genetic editing, etc. A probiotic is defined as live microorganisms that are intended to have health benefits when consumed or applied to the subject. In some embodiments the probiotic may include bacteria and yeast from the groups *Lactobacillus*, *Bifidobacterium*, or *Saccharomyces boulardii*. In one embodiment the probiotic may be *Lactobacillus plantarum*.

In another aspect, the treatment is administered to the patient for at least 1 week, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks, at least 16 weeks, at least 17 weeks, at least 18 weeks, at least 19 weeks, at least 20 weeks, at least 21 weeks, at least 22 weeks, at least 23 weeks, or at least 24 weeks.

In another aspect, the system and methods disclosed herein may be used to evaluate a treatment of the subject suspected of having ASD, inflammation, or autoimmunity. To evaluate the efficacy of a treatment in a subject suspected of having ASD, inflammation, or autoimmunity, a first evaluation of the subject may be performed in advance of the treatment, followed by a second evaluation conducted after administering a treatment, and finally comparing the first evaluation to the second evaluation. In one embodiment, in the first evaluation of the subject, a first measure of CO may include receiving a first level of blood CO (SpCO) in the subject and in the second evaluation of the subject, a second measure of CO may include receiving a second level of blood CO (SpCO) in the subject. The first and second SpCO values may be used to indicate or predict levels of at least one of a first biomarker and levels of at least one of a second biomarker. The levels of at least one of a first biomarker and levels of at least one of a second biomarker may indicate a diagnosis or change in diagnosis, a treatment or change in response to a treatment, or a subgroup or change in a subgroup of the subject.

Unless otherwise specified or indicated by context, the terms "a", "an", and "the" mean "one or more." For example, "a molecule" should be interpreted to mean "one or more molecules."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference, for all purposes, to the same extent as if each reference were individually and specifically indicated to be incorporated by reference and were set forth in its entirety herein.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

Example

Introduction

Autism Spectrum Disorder (ASD) is an intricate neurodevelopmental disorder featuring social deficit and repetitive restrictive behaviors. According to the latest Centers for Disease Control and Prevention (CDC) release, the prevalence of ASD has rapidly increased to 1 in 54 children in the USA. Inflammatory mechanism, autoimmunity, and gut-brain axis have been implicated in the etiology and pathogenesis of ASD. Anti-inflammatory agents, conventional immunotherapy and probiotics have shown promising therapeutic effects to modify the core symptoms of ASD.

Inflammatory mechanisms were widely reported to be linked with ASD and its severity. Previous studies found that inflammatory cytokines were significantly elevated in ASD subjects when compared with healthy controls. Meantime the brain injury and inflammatory markers, glial fibrillary acidic protein (GFAP), myelin basic protein (MBP), and S100 calcium-binding protein B (S100B), were also found to be more enriched in ASD children than healthy controls; these brain injury markers and cytokine release trigger glial cell activation and inflammatory process in the brain. S100B was significantly positively correlated with the severity of problem behaviors in our previous report. However, these serum markers are not readily used in clinical settings due to a lack of further validation and standardization. Furthermore, the cost of performing such assays are high for individuals.

Autoimmunity-mediated neuroinflammation and systemic inflammation were also widely reported in this field. Several serum autoantibodies have been detected in individuals with ASD, which could cause systemic inflammation and change in the tight-junctions of the blood-brain barrier (BBB), leading to permeability disruptions. Among the autoantibodies reported, anti-endothelial cell antibodies (AECA) were first reported in ASD individuals by Connolly A M et al. Later a study reported that AECA levels correlate with ASD severity. Endothelial cells, including those in the brain, maybe targeted by AECAs to cause damage resulting in vasculitis. Pediatric Autoimmune Neuropsychiatric Disorders Associated with Streptococcal Infections (PANDAS) was found to have significant overlap with ASD. Cunningham Panel included autoantibodies Anti-Dopamine Receptor D1 (Anti-D1), Anti-Dopamine Receptor D2L (Anti-D2L), Anti-tubulin, and Anti-lysoganglioside GM1 (Anti-GM1), as well as an assay of calcium calmodulin-dependent protein kinase II (CaMK II) activity, was studied in ASD cohort and found to be related to ASD severity and response to intravenous immunoglobulin (IVIg) treatment. The D1 and D2L receptors are involved in many aspects of functioning, including but not excluded to memory, motor, and impulse control. Tubulin plays a central role in maintaining neuron structure and is important for normal brain function. GM1 is involved in behavioral pathways in the brain. Finally, CaMK II plays a role in many functions but is key in learning and memory. The antibodies could be related to autoimmune encephalitis and disease severity. These autoantibodies are also not readily applied in routine practice due to high cost and lack of further validation.

Heme oxygenase-1 (HO-1) cleaves hemoglobin to form carbon monoxide (CO), biliverdin, and iron. HO-1 is a well-studied anti-inflammatory enzyme known to be elevated in various inflammatory disorders and targeting HO-1 and CO has been proposed a therapeutic modulation for inflammation. Measuring carboxyhemoglobin (SpCO) level via a finger sensor of a pulse CO-oximeter is an extremely easy, quick, and non-invasive test. Recent studies of the Coronavirus disease 2019 (COVID-19) have hypothesized that oxidative stress may be a factor in causing inflammation along with an increase in CO levels. This relationship between SpCO level and inflammation may also be present in ASD, as oxidative stress and inflammation have been recorded, which is worthy of exploring.

Gut microbiome dysbiosis and inflammatory mechanisms were reported to have a strong correlation in the pathogenesis of ASD. We previously reported a high correlation between gut microbiome dysbiosis and cytokine dysfunction ($n_{ASD}=45$; $n_{Healthy\ Control,\ HC}=41$). Probiotics administrations were reported to have anti-inflammatory effects and therapeutic potential in both animal and human studies. *L. plantarum* was found to stimulate serotonin and dopamine levels in animal studies and improve ASD behaviors in human studies. It is known that oxytocin (OT) signaling may serve as a critical link in the gut-brain axis, which may be regulated by the supplementation of probiotics, OT was widely reported to have anti-inflammatory effects and therapeutic potential, measuring OT level is of importance to monitor inflammation, ASD core symptoms and treatment response.

To further our understanding and clinical application of the concept of inflammation, autoimmunity, and gut-brain axis in the ASD population, we conducted this post-hoc exploratory analysis study of our recently published double-blind, randomized, placebo-controlled clinical trial with multiple related secondary outcome measurements to fill the gaps in the field. We explored the easily applied SpCO measuring HO-1, and the correlations with autoantibodies including AECA and Cunningham Panel, inflammatory serum markers including cytokine interleukin-1β (IL-1β) and brain injury markers (S100B, GFAP, MBP), OT serum level, microbiome profile, GI symptom severity, ASD core symptom severity and the treatment response to probiotics *L. plantarum* from reported clinical trial. We aim to assess the potential value of using easily administered pulse CO-oximeter by comparing the serum markers for early screening, diagnosis and subgrouping ASD, and guide corresponding treatment options which have already some reported efficacy, to facilitate early intervention and improve prognosis of ASD individuals.

Methods

Study Design and Participants

The original clinical trial design, protocol, randomization, blinding, participant eligibility, and intervention were well described in our previous publications: Kong X-J, et al. Probiotic and Oxytocin Combination Therapy in Patients with Autism Spectrum Disorder: A Randomized, Double-Blinded, Placebo-Controlled Pilot Trial. Nutrients. 2021; 13:1552. and Kong X-J, et al. Probiotics and oxytocin nasal spray as neuro-social-behavioral interventions for patients with autism spectrum disorders: a pilot randomized controlled trial protocol. Pilot Feasibility Study. 2020; 6:20, both incorporated by reference herein in their entirety and for all purposes.

In this study, we conducted an exploratory analysis and included all 35 subjects aged 3-25 with diagnosis of ASD from our phase 1 randomized, double blinded and placebo-controlled probiotics trial. Of the 35 subjects, the probiotics group received oral probiotics PS128 (*Lactobacillus planta-*

*rum* PS128, a total of $6\times10^{10}$ CFUs per day) while the placebo group received oral placebo (microcrystalline cellulose) for a total duration of 16 weeks. The study was conducted according to the guidelines of the Declaration of Helsinki. Ethical approval of the original study was issued by the Internal Review Board (IRB) of Massachusetts General Hospital (2017P001667) and this secondary use IRB (2020P004102). The original clinical trial was registered through ClinicalTrials.gov with the identifier NCT03337035 (registered Nov. 8, 2017; https://clinicaltrials.gov/ct2/show/NCT03337035). Written informed consent was obtained from either competent adult subjects, parents, or legal guardians of children and adults with cognitive impairment according to the IRB requirements. A timeline is presented in FIG. 1 to illustrate the sample size, assessed variables, and dropouts at each stage of the study.

Outcome Measures for the Analysis

Pulse Oximetry Measurements

SpCO was measured via pulse CO-oximetry which is a noninvasive technique that assesses the levels of various blood constituents, including SpCO, oxygen saturation ($SpO_2$), and heart rate (HR). Measurements with the Masimo devices were taken by placing a sensor on the subject's index or ring finger on either the right or left hands. This measurement was done in a clinical examination room over a two-minute period, where SpCO was recorded at 0 minutes and again at 2 minutes. These two records were then averaged for analysis. This measurement was collected during the primary trial but not included in previous publication. Based on previous studies of SpCO levels in cigarette smokers and non-smokers, non-smokers have been found to have SpCO values of <1.5%; as a result, a percentage of ≥2% is denoted as positive while a measurement of <2% is denoted as negative.

Blood Sample Collection and Circulating Serum Biomarker Measurements

Blood drawn and the serum processed during the original trial week 0 and week 16, was used to measure AECAs by an ELISA kit manufactured by R&D Systems Inc. (Minneapolis, MN, USA) following the manufacturer-supplied protocol, and sent to Moleculera labs (Oklahoma City, OK) for the Cunningham Panel measurement following their instruction. These two blood measurements were not included in our previous publication. In this study, we denote positive results for CaMKII activity, anti-Tubulin, anti-D1, anti-GM1, and anti-D2L using cutoffs cited by the testing facility (Cunningham Panel, Moleculera Labs). In brief, positive titer result cutoffs are determined based on the mean titer results of the healthy study population from the study conducted by Chain et al., such that anti-D1 titers with values of 2000 or higher, anti-D2L with values of 8000 or higher, anti-GM1 with values of 320 or higher, and anti-tubulin with values of 1000 or higher are considered positive results. Similarly, a positive result is denoted for CaMKII activation based on its activity with values of ≥130% above the basal mean activation rate. Circulating serum OT, MBP, GFAP, S100B, IL-1β measurements were described in our previous publication and designations of positive and negative cutoffs relevant to the current FIG. 2 for S100B, MBP, and IL-1β are determined based on whether detectable levels were identified in our subject population.

Other Outcome Measurements Included in this Analysis

GI symptom severity assessments by the validated GSI and the Bristol Stool Chart; Social Responsiveness Scale (SRS), Aberrant Behavior Checklist second edition (ABC-2), Clinical Global Impression (CGI), Stool Sample Processing, DNA extraction and sequencing analysis were well described in our previous publication (Kong X-J, et al. Probiotic and Oxytocin Combination Therapy in Patients with Autism Spectrum Disorder: A Randomized, Double-Blinded, Placebo-Controlled Pilot Trial. Nutrients. 2021; 13:1552, incorporated by reference herein in its entirety and for all purposes).

Bioinformatics Processing and Statistical Analysis

The analyses of a dataset generated from a double-blinded, placebo-controlled probiotic clinical trial was performed for the present study. Fecal 16S sequence reads were processed through Biobakery Workflows (v0.13.2) with default parameters using the VSEARCH-based method. Assignment of OTU taxonomies were done using the Greengenes database (v13.8) with 97% sequence similarity. The resulting reads were filtered using a prevalence threshold of 0.0001 and an occurrence threshold of 10%. Subsequently, the abundance data was transformed into relative abundances for downstream analysis. Linear discriminant analysis effect size (LEfSe) was used to evaluate differentially abundant microbiota relative abundances both at baseline and post-treatment using a one-against-all strategy for multiclass analysis with statistical significance considered at α=0.05 and a threshold for the logarithmic LDA score of 2.0. The 16s fecal microbiome sequencing data presented in this study are openly available in the Sequence Read Archive (SRA) database of The National Center for Biotechnology Information at https://www.ncbi.nlm.nih.gov/bioproject/PRJNA675093, with accession number PRJNA675093. For assessment of correlations by placebo and probiotic treatment group effects, the absolute change between baseline (0-weeks) and post-probiotic intervention (16-weeks) were calculated for pulse oximetry, and serum inflammatory markers features. Serum autoantibody titers were log 2-transformed and correlational analysis was conducted using Kendall's rank correlation. Adjustment for multiple comparisons was not performed as each test was conducted according to pre-specified hypotheses. A table of all assessed correlations are provided in Table 1:

TABLE 1

| Overview of all assessed correlations. | | | | | |
|---|---|---|---|---|---|
| | Baseline Cunningham Panel titers | Baseline SRS | Baseline ABC | Baseline CGI | Baseline GFAP |
| Baseline SpCO | * | *X | | | |
| Change in SpCO | *X | * | | | |
| Change in ASD severity (CGI/ABC/SRS) | *X | | | | |

TABLE 1-continued

| | Baseline Cunningham Panel titers | Baseline SRS | Baseline ABC | Baseline CGI | Baseline GFAP |
|---|---|---|---|---|---|
| Change in GSI | | *X | | | *X |
| Baseline α diversity | | *X | * | * | |
| Change in α diversity | | *X | *X | *X | |
| Change in OT | | * | * | *X | *X |
| Change in GFAP | | * | *X | * | |

*Starred cells indicate all assessed correlations and "X" indicates a significant correlation identified within the present dataset.

Results

We conducted exploratory analysis based on a cohort of 35 children with ASD aged $10.26 \pm 4.78$ years, which included 26 males and 9 females. The maternal age at childbirth is $32.96 \pm 4.9$ years. Each participant was assessed for their GI symptom severity via the GSI, which suggested scores of $2.86 \pm 1.77$. Furthermore, the severity of ASD symptoms were assessed via the ABC-2, SRS, and CGI. The ABC-2 yielded total T scores of $275.06 \pm 32.29$, the SRS gave a total score of $113.8 \pm 36.96$, and the CGI-S gave scores of $5.11 \pm 1.02$. Detailed participant demographics and characteristics are summarized in Table 2. The 35 subjects were randomized assigned into two groups: probiotics group and placebo group. There were no significant differences between two groups in term of age, sex, ASD severity, and GSI as reported.

TABLE 2

Summary of participant demographics and clinical characteristics.

| Demographic Feature | All (n = 35) |
|---|---|
| Age (years) | 10.26 ± 4.78 |
| Sex (n) | |
| Male | 26 |
| Female | 9 |
| Maternal age | 32.96 ± 4.9 |
| GSI Index | 2.86 ± 1.77 |
| ABC-2 Total Score (T) | 275.06 ± 32.29 |
| SRS Total Score | 113.8 ± 36.96 |
| CGI-S | 5.11 ± 1.02 |

Figure 2:
FIG. 2 shows an overview of proportion of participants with detected positive SpCO and serum inflammatory markers at baseline. For SpCO, a measured percentage of $\geq 2$ is denoted as "positive"; for titers of anti-Dopamine Receptor D1, D2L, anti-Lysoganglioside GM1, anti-Tubulin, and activity of CaM Kinase II of baseline, normal levels are denoted as "negative" and both borderline and elevated levels are denoted as "positive;" all remaining indices are denoted based on the absence ("negative") or presence at detectable levels ("positive"). GFAP and OT were not included due to lack of reference for the determination of cutoff values.

We summarized the baseline levels of SpCO, serum autoantibodies, and serum inflammatory markers in this cohort. Based on such results, we found that the positive rate of the respective measurements are common and widely distributed (FIG. 2). Specifically, CaM kinase II and anti-tubulin are among the highest at 94.4% of subjects with elevated titers, followed by AECA with 82.6% of subjects with positive measurements, anti-dopamine receptor D1 (77.8%), SpCO (64.7%), S100B (64%), and anti-lysoganglioside GM1, and anti-dopamine receptor D2L both with 27.8% of subjects with elevated titers, IL-1β (24%), MBP (16%). Of note, GFAP and OT were not included due to lack of reference for the determination of cutoff values.

Figure 3:
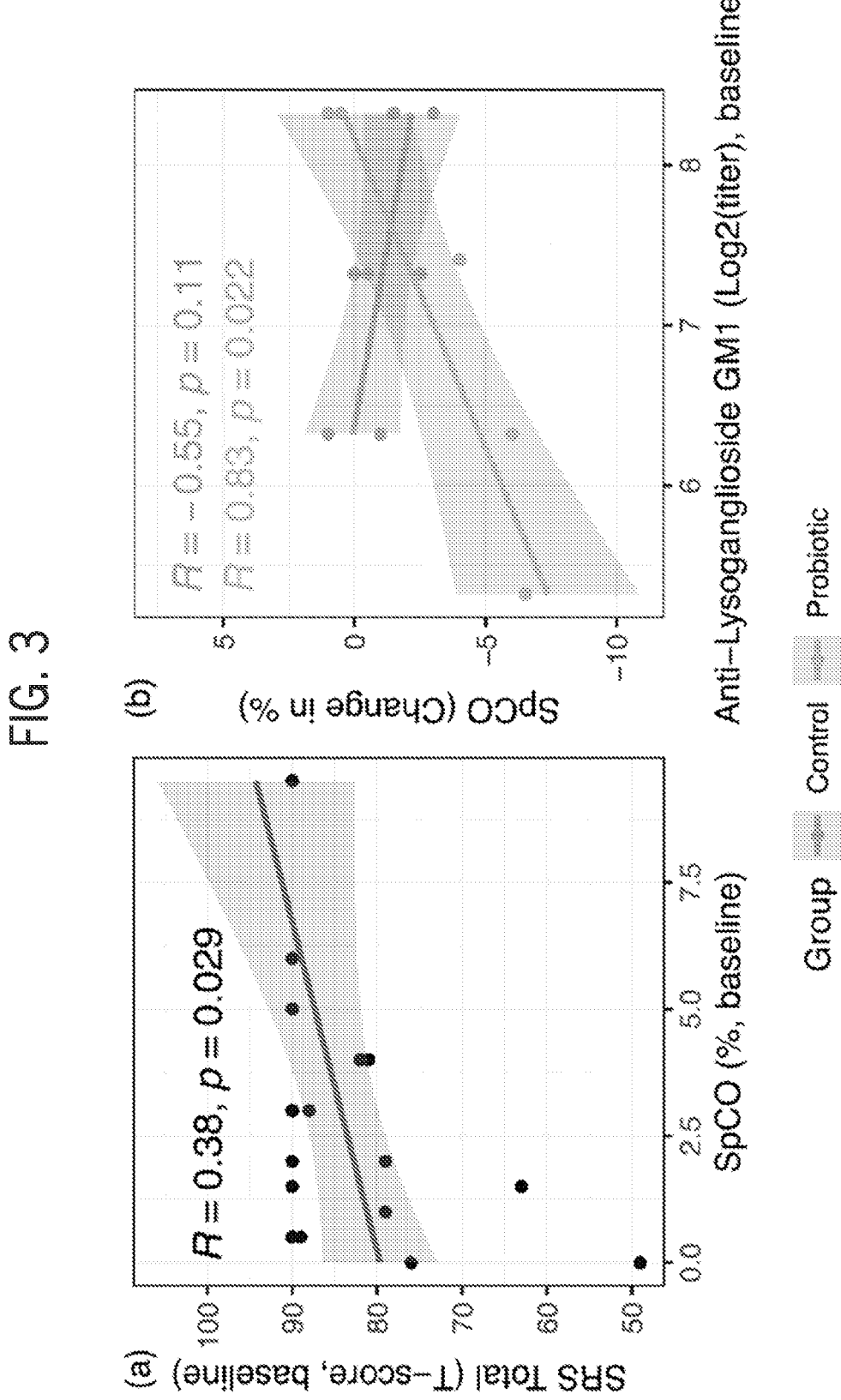
FIG. 3 shows correlations between SpCO, ASD socio-behavioral severity, and autoantibody titers at baseline and post-intervention with either probiotics (blue) or placebo (red). Shown correlations are based on Kendall's correlation using a significance cutoff of $\alpha=0.05$. Panel (a) shows that SRS Total T-scores are positively correlated with SpCO for all subjects at baseline. Panel (b) shows the absolute change in SpCO between weeks-0 and -16 is positively correlated with anti-lysoganglioside GM1 log-titers in those receiving the probiotic treatment.

We found that the baseline SpCO was positively correlated with baseline SRS total scores (FIG. 3A, R=0.38, P<0.05), while the absolute change in SpCO post-intervention by treatment group was found to be positively correlated with baseline titers of anti-lysoganglioside GM1 among subjects receiving the active probiotic but not among those receiving the placebo control (FIG. 3B, $R_{Probiotic}=0.83$, $P_{Probiotic}<0.05$), which suggests that subjects with lower baseline anti-GM1 titers show a trend of decreasing SpCO post-probiotic intervention.

Figure 4:
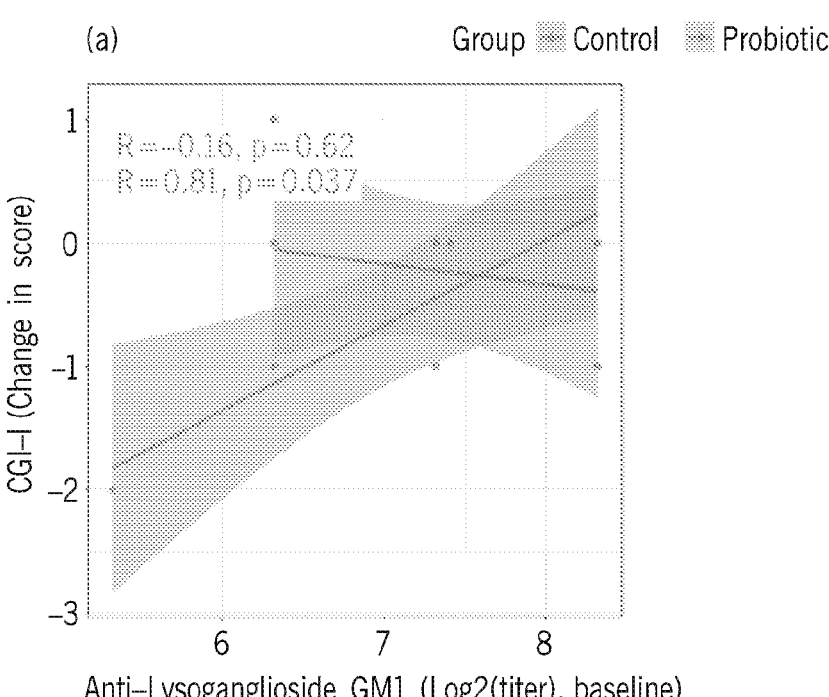
FIG. 4 shows correlations between serum autoantibody titers, inflammatory markers, and ASD severity scores, at baseline and post-intervention. Shown correlations are based on Kendall's correlation using a significance cutoff of $\alpha=0.05$. Panel A shows the correlations of baseline titers of anti-lysoganglioside GM1 with CGI-I (change in score), Panel B shows correlation of baseline titers of anti-lysoganglioside GM1 with ABC-2 total score (Change in raw score), and Panel C shows correlation of baseline titers of anti-lysoganglioside GM1 with ABC-2 stereotypic behavior (Change in T score).
Figure 4:
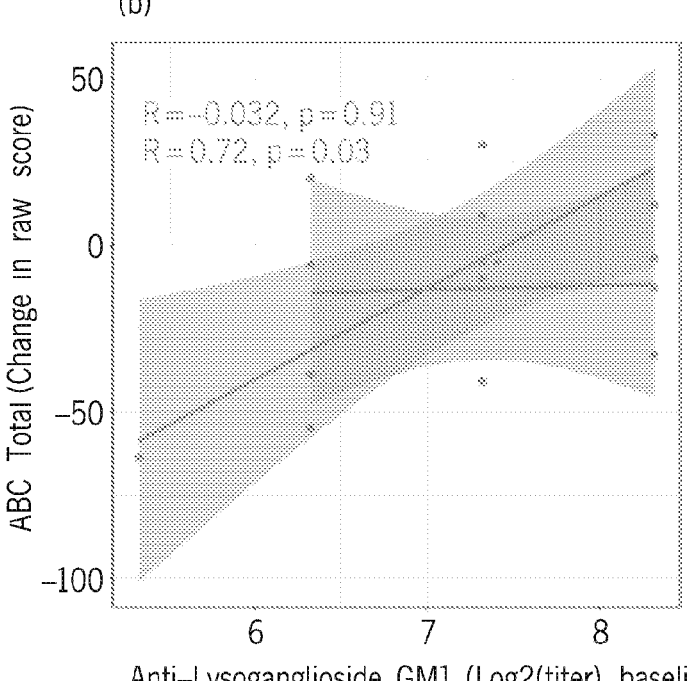
Figure 4:
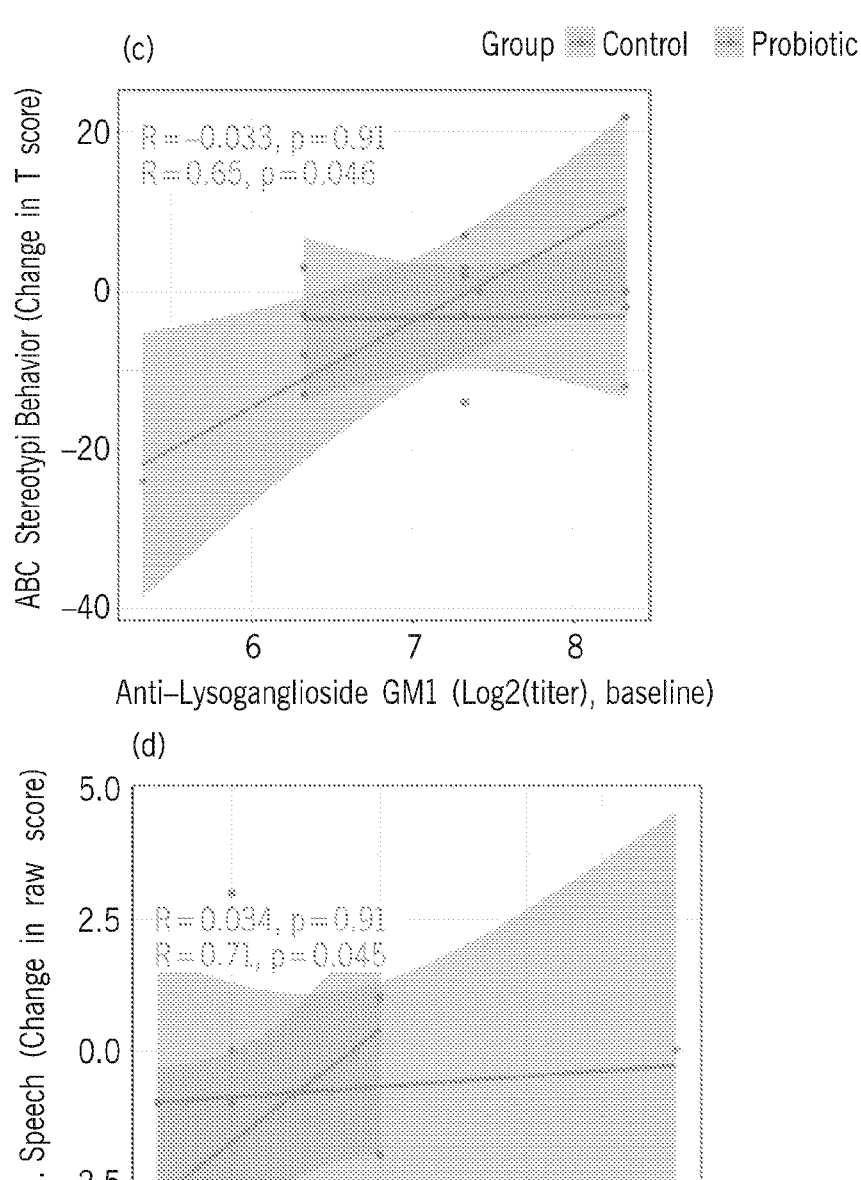
Figure 4:
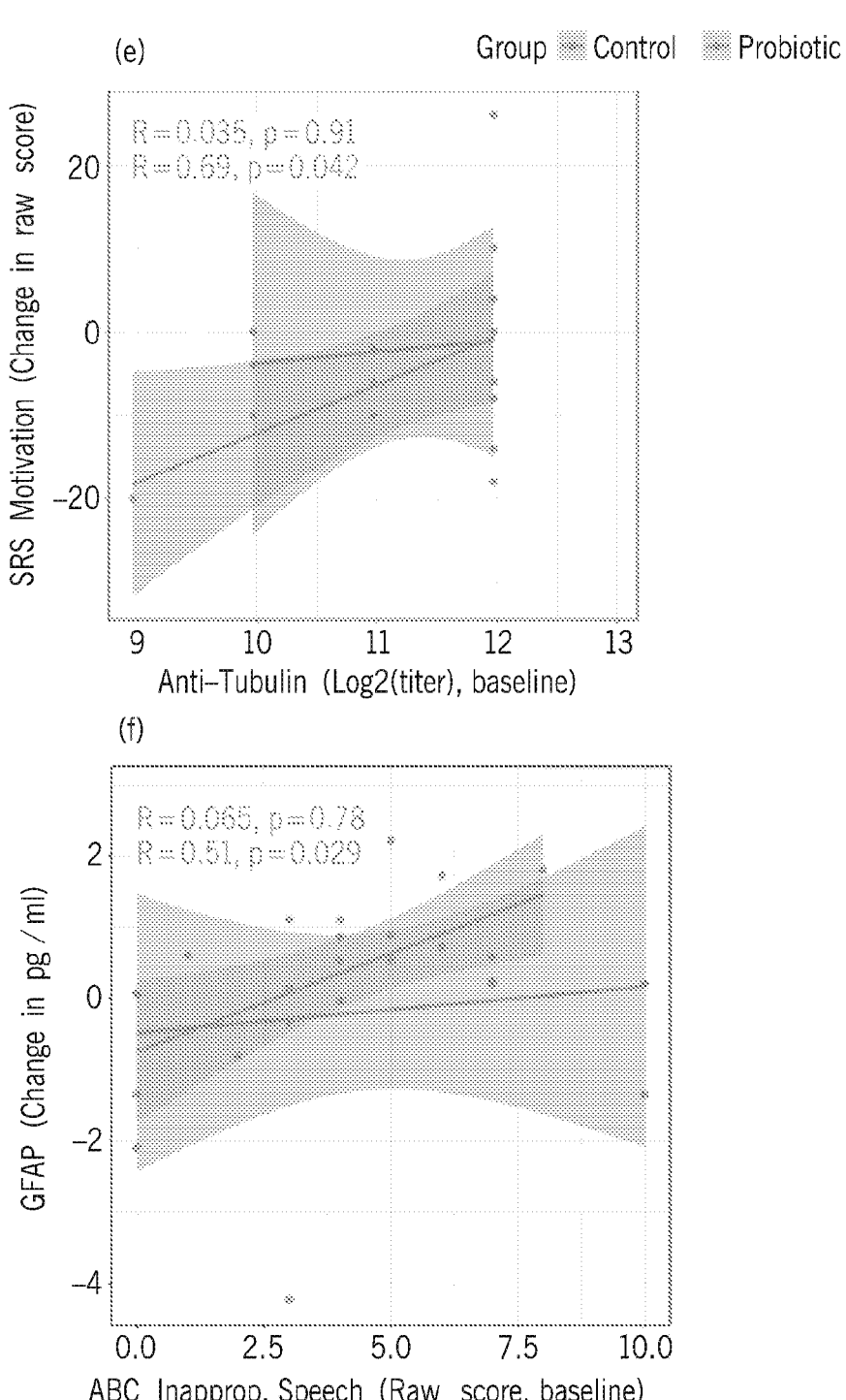

The absolute change in CGI-I, ABC-2 total score and ABC-2 stereotypic behavior sub-score between 0-weeks and 16-weeks were found to be positively correlated with baseline titers of anti-lysoganglioside GM1 in the probiotics-treated group but not in the placebo-treated group (FIG. 4A-C, $P_{Probiotic}<0.05$). Furthermore, the change in ABC-2 inappropriate speech sub-score was found to be positively correlated with baseline titers of anti-dopamine receptor D1 in the probiotics-treated group but not in the placebo-treated group (FIG. 4D, $P_{Probiotic}<0.05$). Similarly, the change in SRS motivation sub-score was found to be positively correlated with baseline titers of anti-tubulin among the probiotics-treated group but was not observed in the placebo-treated group (FIG. 4E, $P_{Probiotic}<0.05$). Lastly, the change in serum GFAP concentration was found to be positively correlated with baseline scores of ABC-2 inappropriate speech sub-score among subjects receiving the active probiotic but not among those receiving the placebo control (FIG. 4F, $P_{Probiotic}<0.05$).

Figure 5:
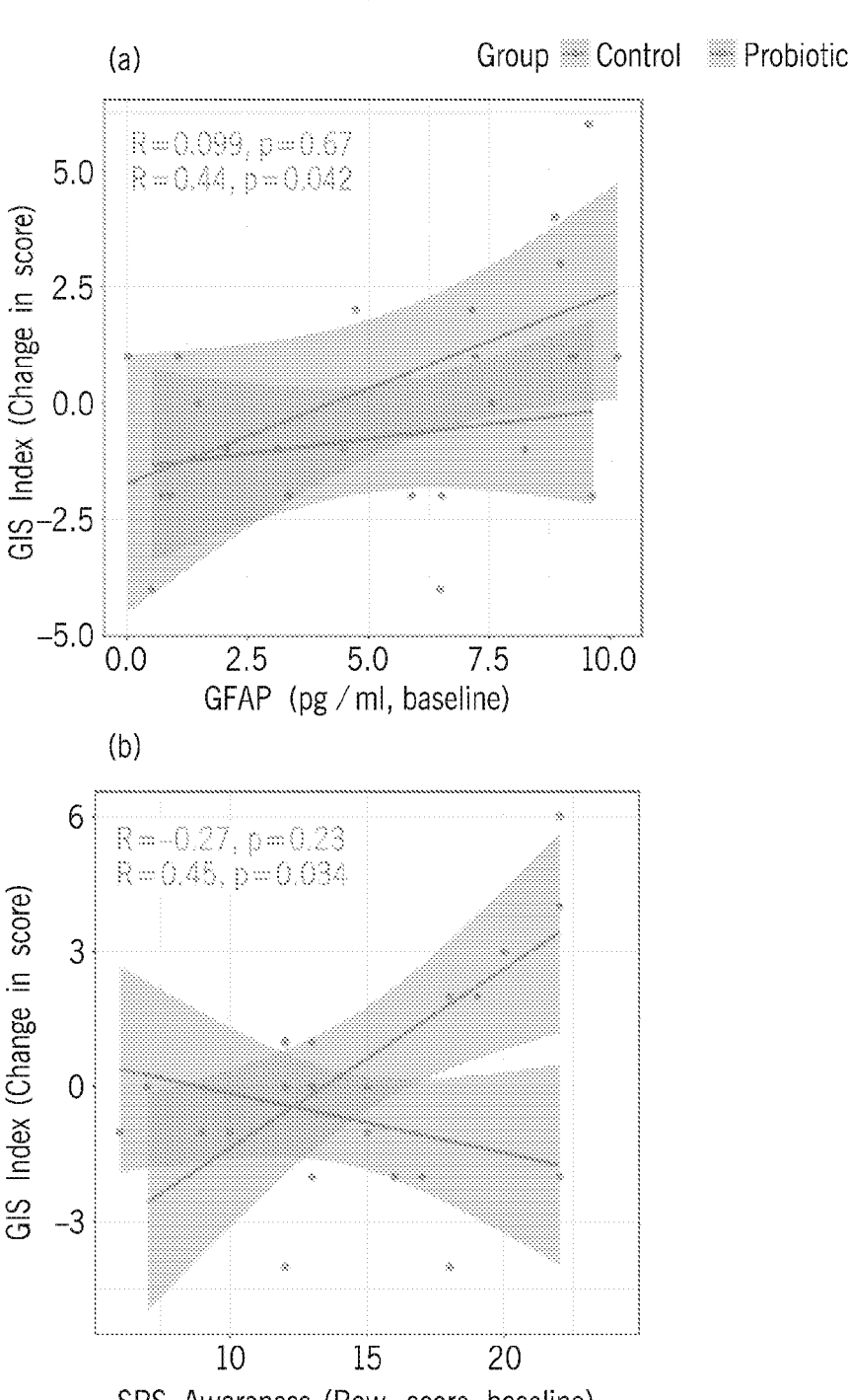
FIG. 5 shows GSI change and its correlations with inflammatory marker and ASD severity.
Figure 5:
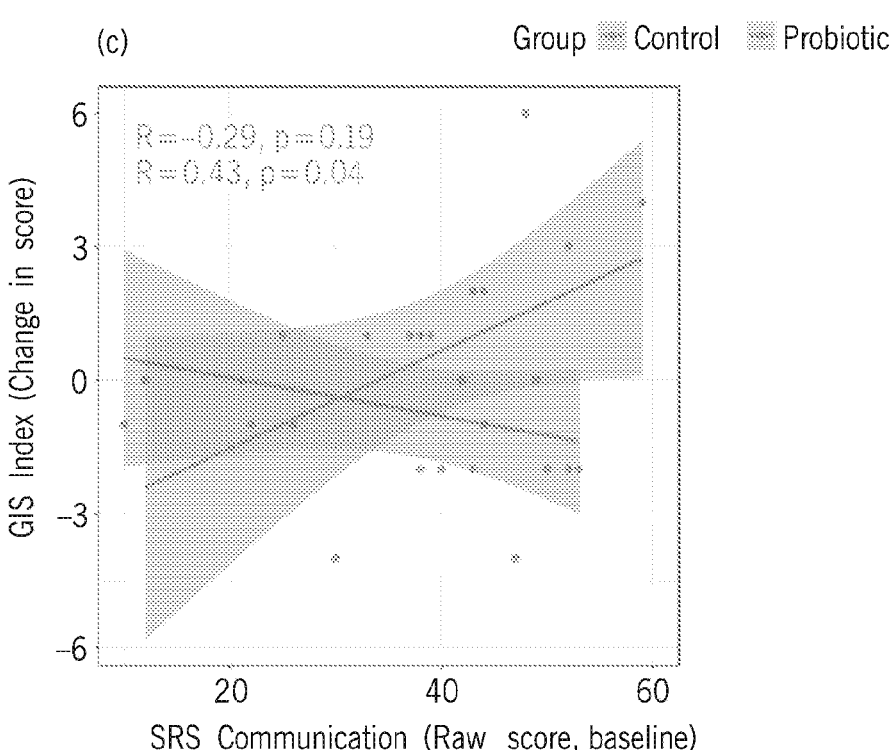

The change in GSI index among subjects receiving the active probiotic was found to be positively correlated with baseline GFAP concentration (FIG. 5A; $R_{Probiotic}=0.44$, $P_{Probiotic}<0.05$), SRS awareness (FIG. 5B; $R_{Probiotic}=0.45$, $P_{Probiotic}<0.05$), and SRS communication sub-score (FIG. 5C; $R_{Probiotic}=0.45$, $P_{Probiotic}<0.05$). However, these corresponding correlations are not found to be significant among the subjects receiving the placebo control (FIG. 5).

Figure 6:
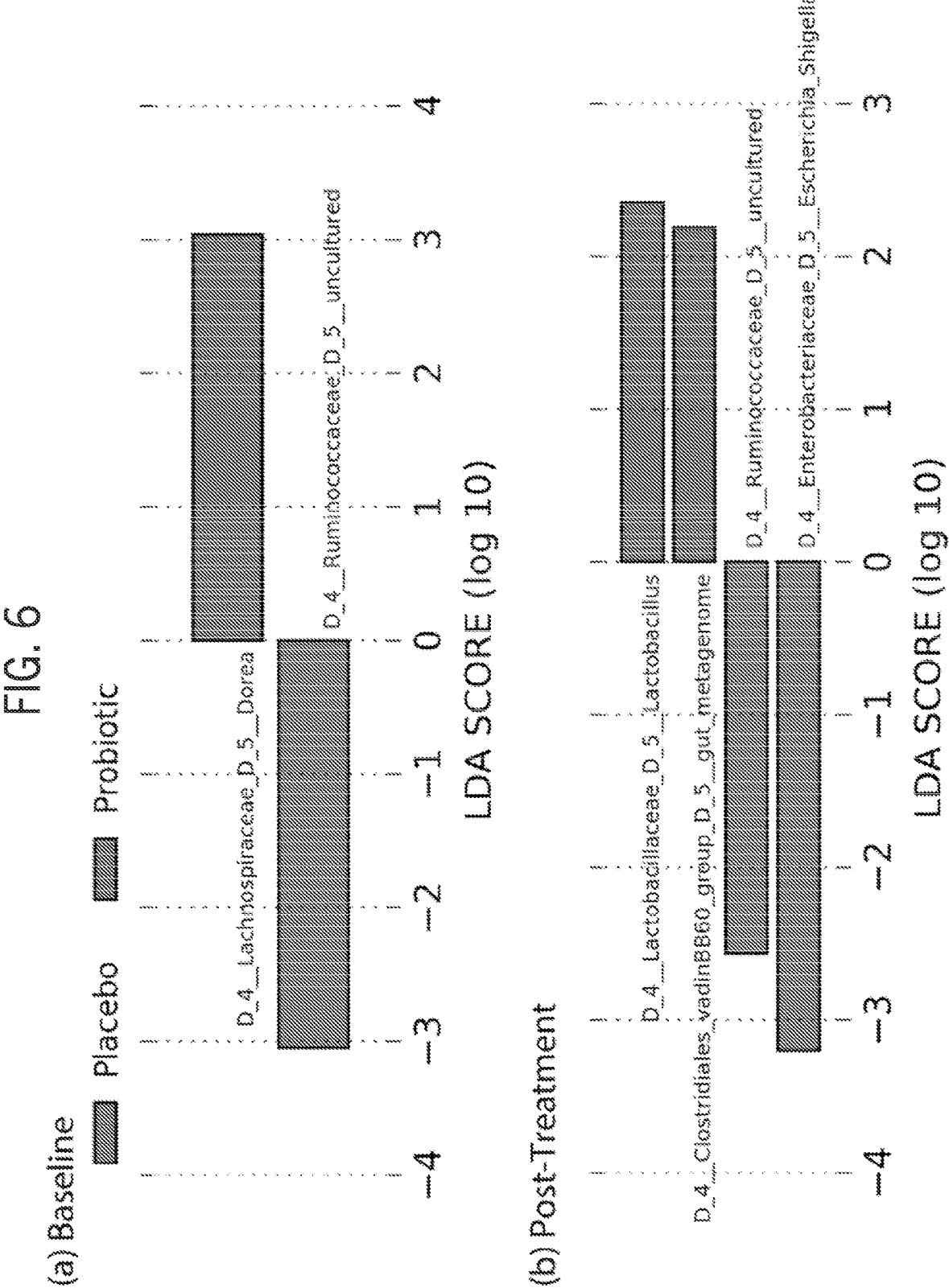
FIG. 6 shows differentially enriched microbiota between placebo and probiotic groups. Analyses was conducted at (a) baseline and (b) post-treatment for both groups via LEfSe.

Assessment of differentially enriched microbiota by group both at baseline and post-intervention suggested several significant genus-level differences in relative abundance. The presented LDA scores of each microbiota with respect to the interventional groups were found to be significantly different at both baseline (FIG. 6A) and post-intervention (FIG. 6B) between probiotics interventional group and placebo control group (FIG. 6, P<0.05).

Figure 7:
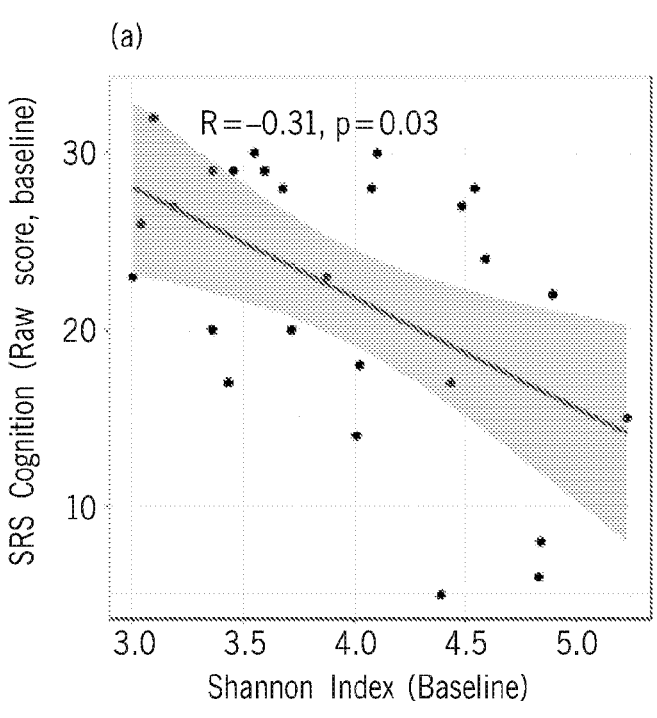
FIG. 7 shows correlations between point measurements and change in Shannon index, OT, GFAP, ASD severity, and autoantibody titers at both baseline and post-intervention.
Figure 7:
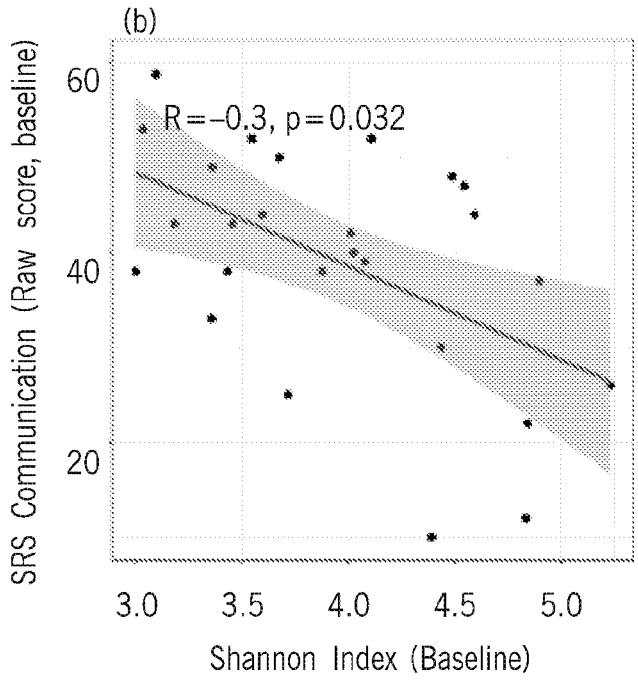
Figure 7:
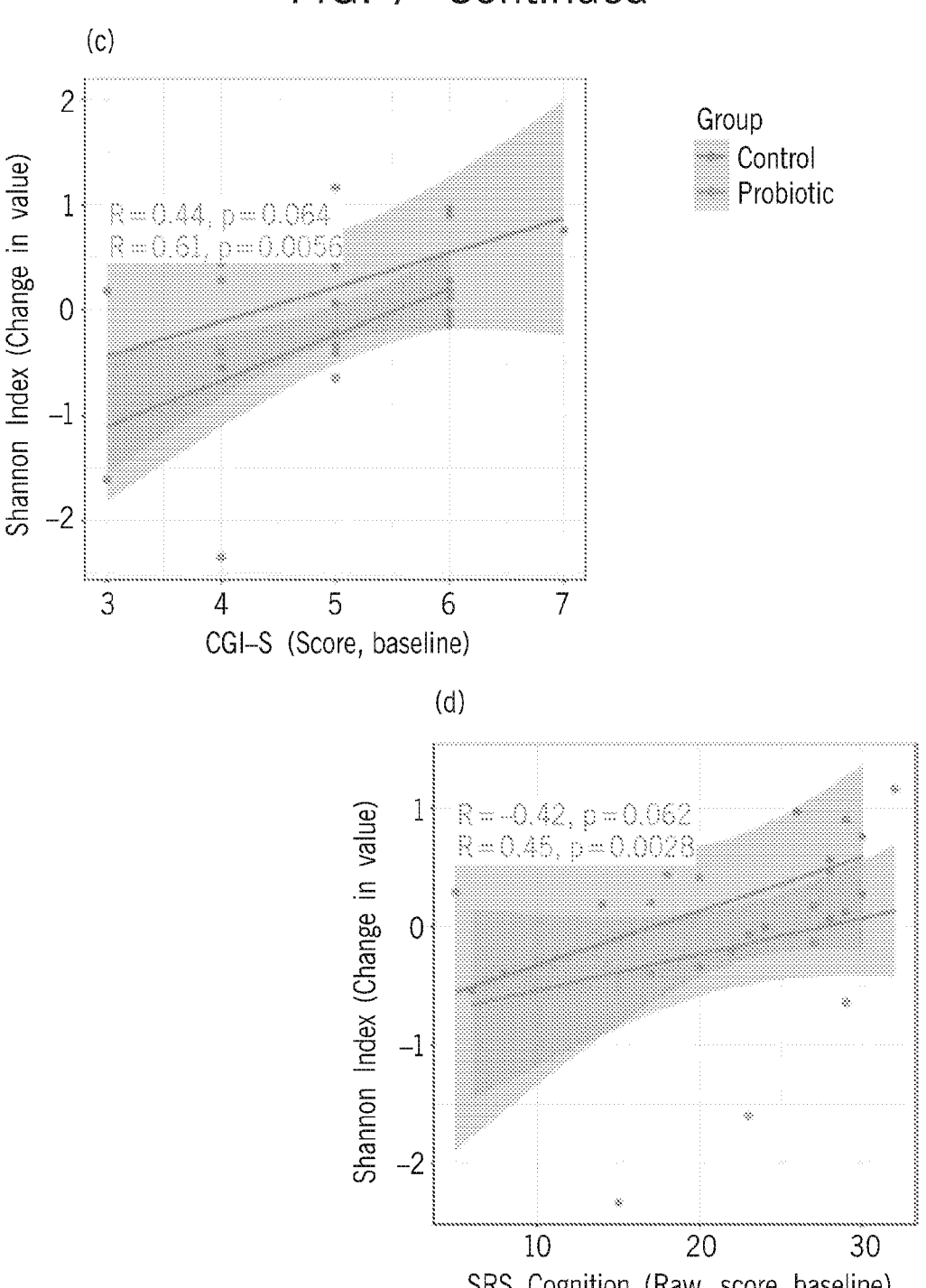
Figure 7:
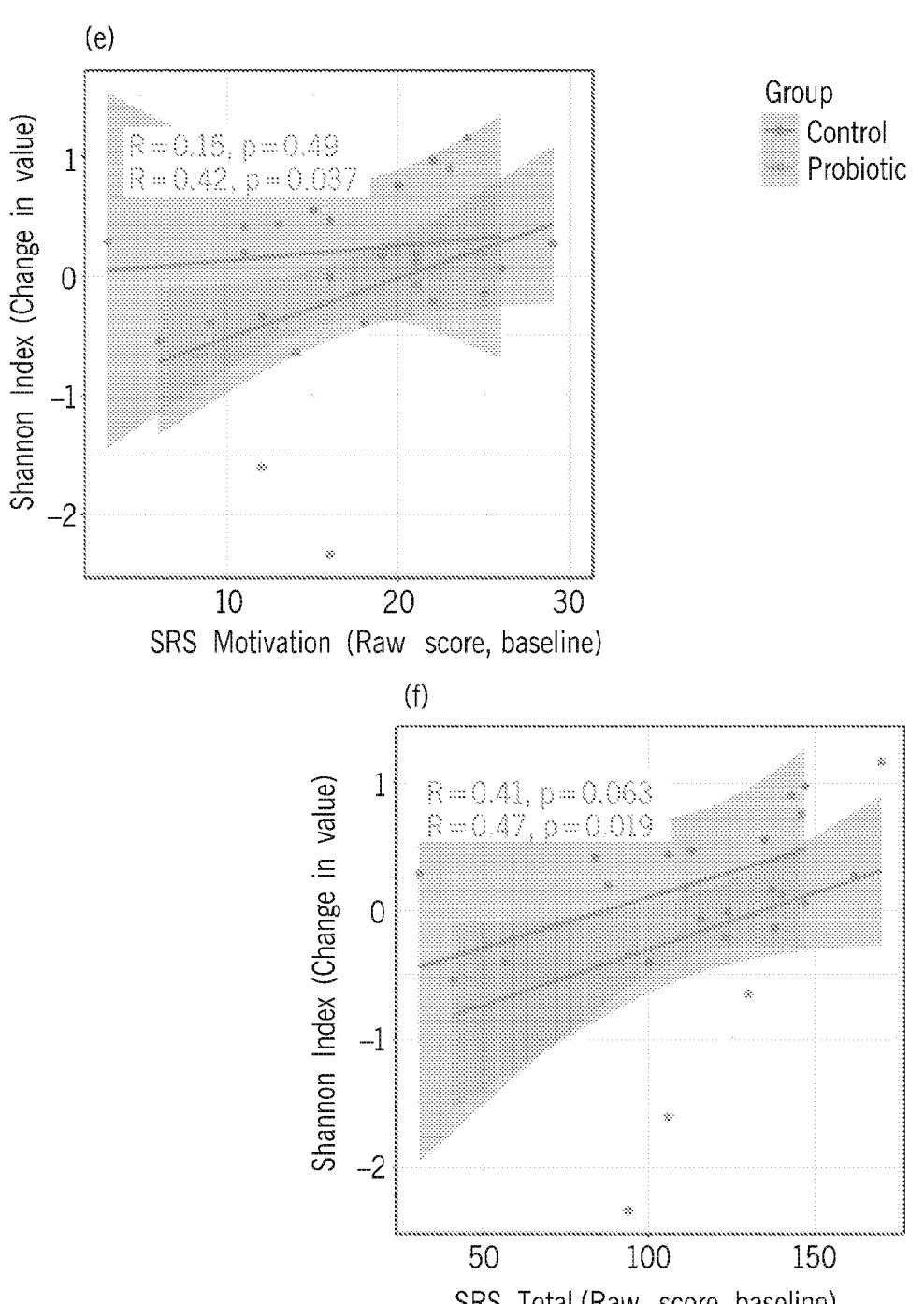
Figure 7:
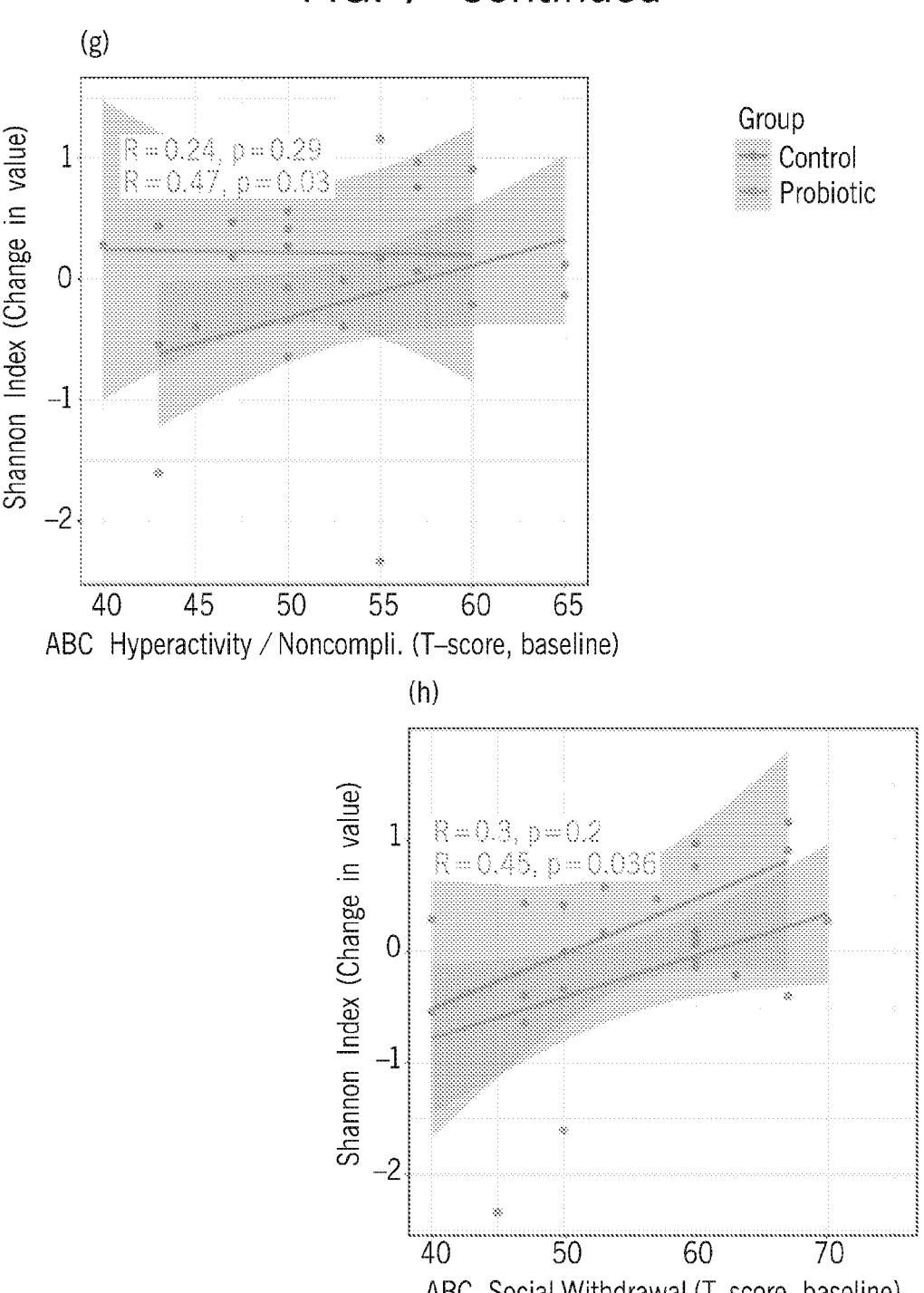
Figure 7:
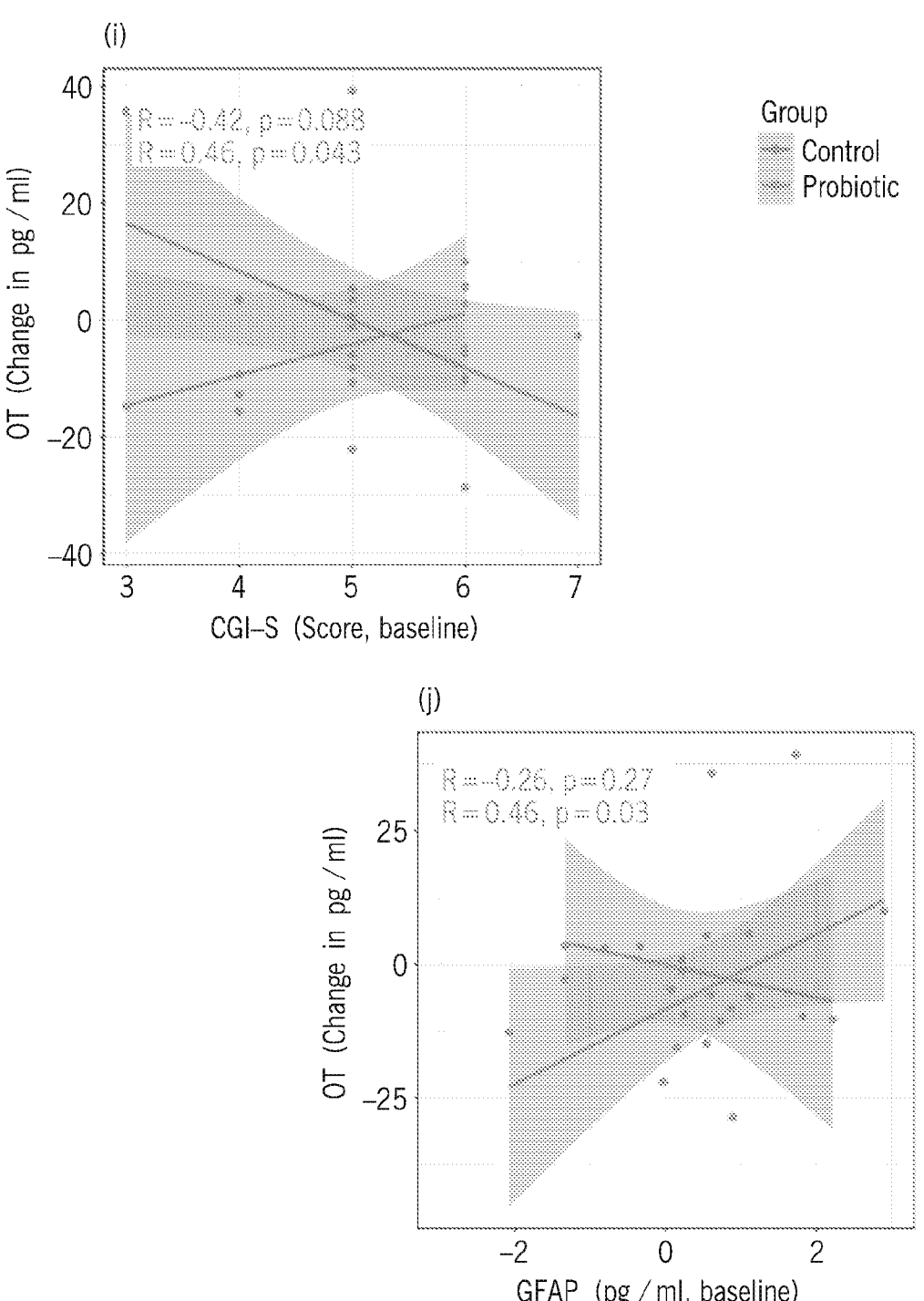

Baseline Shannon index was found to be negatively correlated with baseline scores of SRS cognition and SRS communication (FIG. 7A-B; R=-0.31, P<0.05 and R=-0.3, P<0.05, respectively). The change in Shannon index was found to be positively correlated with baseline CGI-S, SRS total score, SRS sub-scores, including cognition and motivation, and ABC-2 sub-scores, including hyperactivity/non-compliance and social withdrawal among subjects receiving the active probiotic (FIG. 7C-H, $P_{Probiotic}<0.05$). The change in OT was found to be positively correlated with baseline measurements of CGI-S and GFAP among subjects receiving the active probiotic (R=0.46, P<0.05 and R=0.46, P<0.05, respectively) but these correlations are not observed among controls (FIG. 7I-J).

In the present study, we conducted an exploratory analysis to examine and compare multiple inflammatory markers including SpCO measured by pulse CO-oximetry, several serum autoantibodies, cytokines, brain injury markers, OT level, gut microbiome composition, the correlations among them, and their correlations with ASD core symptom severity, GI symptom severity and the treatment response to the probiotic strain *L. plantarum* in randomized, double-blinded, placebo-controlled clinical trial. We found that positive measurements of inflammatory/autoimmunity markers were common among the study cohort but with varying prevalence: CaMKII and anti-tubulin are among the highest at a positive rate of 94.4%, followed by AECA with a rate of 82.6%, anti-D1 titer 77.8%, SpCO 64.7%, S100B 64%, anti-lysoganglioside GM1 and anti-D2L titer both 27.8%, IL-1β 24%, MBP 16%, which indicated that auto-immunity to tubulin, D1, AECA and related ongoing *strep-tococcus* infection are extremely common in this ASD cohort, autoantibodies to lysoganglioside GM1 and D2L are with much lower presence, while cytokine IL-1β and brain injury markers such as MBP are even less prevalent. From the previous Cunningham panel related studies indicated that D2L and tubulin correlated to ASD severity. AECA was initially reported present in 30% of the ASD later reported significantly higher than control group and correlated with ASD severity. SpCO measured by pulse CO-oximetry was first explored in ASD population in this study, found to be abnormal in 64.7% of this ASD cohort, which is very close to inflammation rate found in the postmortem brains with multifocal perivascular lymphocytic cuffs contain increased numbers of lymphocytes in ~65% of ASD compared to control brains in males and females, across all ages, in most brain regions.

Interestingly, we first found that the SpCO level was significantly positively correlated with SRS total score at baseline, meaning SpCO could be indicative to ASD core symptom severity; Furthermore, the change of SpCO with intervention was found to be significantly positively correlated with serum GM1 level in probiotics treated group but not in placebo-treated group, which suggest those with lower level of GM1 had a greater improvement in the reduction of SpCO, which is hypothesized to be mediated through PS128 treatment. Similarly, the change in severity of ASD core symptoms by probiotics treatment were also found to be significantly positively correlated with GM1, and additionally with D1 and tubulin levels, these correlations were not found to be significantly associated among subjects of the placebo group. Taken together, these findings suggest that SpCO is a potentially promising autoimmunity/inflammatory biomarker for ASD. Considering the measurement of serum autoantibodies and inflammatory markers are requiring blood draw, not being able to perform in the local conventional labs, expensive price/mostly self-pay, SpCO measured by pulse CO-oximetry has a lot of advantage such as easy, quick (2-min), cheap, on-site, and completely non-invasive. We believe that SpCO could be promising to serve as a screening and diagnostic biomarker to indicate inflammation and autoimmunity therefore subgroup ASD for corresponding further testing or treatments, and also could be used for monitoring treatment outcome as we found in this study. As proposed, same as this promising application in ASD, SpCO could also be a useful quick test for COVID-19 to indicate inflammatory level, monitor severity, and clinical course, similarly for other conditions involved autoimmunity and inflammation. The validation of the application in ASD, specific correlations with each condition and involved pathways are warrant for further studies.

Some studies have shown a correlation between serum level of cytokines and gut microbiome composition, while others reported the serum level of autoantibodies are significantly correlated with ASD severity in both Cunningham panel and AECAs; however, the correlation between autoantibodies and gut microbiome and treatment response with probiotics were not explored in these previous studies. In the present study cohort, the change in GSI showed positive associations against baseline SRS score and GFAP level (P<0.05), suggesting that those with less severe ASD symptoms and lower GFAP levels show a greater extent of reduction in GI symptom severity, which are also potential better respondents to the administered probiotic. Moreover, the baseline gut microbiome alpha diversity was found to be negatively correlated with SRS cognition and communication sub-scores. Additionally, the change in alpha diversity over the intervention course was found to be positively correlated with baseline measurements of CGI-S, ABC-2 and SRS, while being negatively correlated with baseline anti-D2L titer among the probiotic group subjects. These associations, however, are not observed with statistical significance among subjects receiving the placebo control, which likely indicates that the associations between changes in gut microbiome diversity, ASD core symptom severity, and autoantibodies are likely mediated through the supplementation of the probiotic. The abundance changes of certain microbiome with probiotics intervention support the inflammatory mechanism of ASD and anti-inflammatory effect of probiotics. Following intervention, subjects receiving the active probiotic displayed higher abundances of *Lactobacillus*, and an unidentified genus belonging to the Clostridiales vadin BB60 group. Relative to the active probiotic group subjects, those receiving the placebo show higher abundances of an uncultured genus belonging to Ruminococcaceae and higher abundances of *Escherichia-Shigella*. While literature remains largely heterogenous regarding the clinical implications of the differentially abundant unidentified Clostridiales and Ruminococcaceae genera, there has been a suggestion of anti-inflammatory effects through the production of short-chain fatty acids (SCFAs) by the increased *Lactobacillus* genus. Furthermore, the observed higher abundances of *Escherichia-Shigella* within the gut microbiome in subjects receiving the placebo relative to that of the probiotic group suggests that the probiotic supplementation has the potential to suppress the dysbiosis of the *Escherichia-Shigella* genus, which is a well-known opportunistic pathogen and has been shown to be associated with higher severity in constipation among individuals with ASD. These interesting findings of this secondary analysis study displayed the internal relationship of autoimmunity/inflammation, gut microbiome dysbiosis and ASD severity, and the therapeutic role of probiotics in this setting. As mentioned earlier, OT signaling may serve as a critical link in the gut-brain axis, OT was widely reported to have anti-inflammatory effects and therapeutic potential. In this study, we found that the changes of OT was significantly positively correlated in the probiotic group with CGI-S and GFAP at baseline but not with placebo group subjects. OT was reported to be regulated by probiotics, and also interacted with other neurotransmitters and hormones. It's warranted to further explore autoimmunity mediated inflammatory process and gut microbiome dysbiosis, the therapeutic role of probiotics and other anti-inflammatory/immunomodulatory treatments.

There are several limitations of the study that deserve consideration. 1) Despite our adoption of proper recruitment and retention strategies, the participant enrollment and retention for this trial were challenging. This is a secondary analysis study from the parent trial, the sample size is smaller due to limited availabilities of the test results and high dropout rate for blood draw; A small sample size limited the statistical power and further subgroup analysis. 2) The wide age range used in this study resulted in high subject population heterogeneity and potentially variable treatment efficacy. Future studies with a larger sample size and subgroup stratification are warranted. 3) Due to considerable Asian and other minority patients with some cultural and language barriers, in addition to multiple influencing factors on behavioral variabilities, the parent rating of social behavioral scales may be somewhat biased. 4) Adjustments for multiple comparisons was not performed as each correlational test was conducted in the presence of a pre-specified hypotheses. Nonetheless, we acknowledge this as a limitation as the abundance of correlational tests performed may introduce possibilities of false discovery. Despite the several limitations of our analysis strategy, we believe that the presented evidence in the current study is an efficient way to provide suggestive evidence that may serve as preliminary results for future studies in the elucidation of the interactions between ASD symptom severity and biomarkers of inflammation and autoimmunity.

In the present secondary analysis of RCT study, we found a high rate of presence of serum anti-tubulin 94.4%, CaM-KII 94.4%, AECA 82.6%, anti-D1 titer 77.8%, and SpCO 64.7% measured by pulse CO-oximetry in this ASD cohort, we first demonstrated that SpCO was positively correlated with ASD core symptom severity measured by total SRS score (p=0.029), the improvement of SpCO by probiotics was found positively correlated with baseline GM1 level (P<0.05) compared with placebo group. Similarly, ASD core symptom improvement with probiotics was also found to be positively correlated with GM1 and other autoantibodies. These findings indicated that easily administered, non-invasive SpCO a potentially promising autoimmunity and inflammatory biomarker to screen and subgroup ASD and monitor treatment response; The autoantibodies, gut microbiome profile, Serum OT level, GI symptom, and ASD corn symptom severity were all found to be highly correlated in probiotics treated group (P<0.05) compared with placebo-treated group from this study, which warrant further studies to improve ASD early diagnosis and treatment outcome.

Software and Computing

Figure 8:
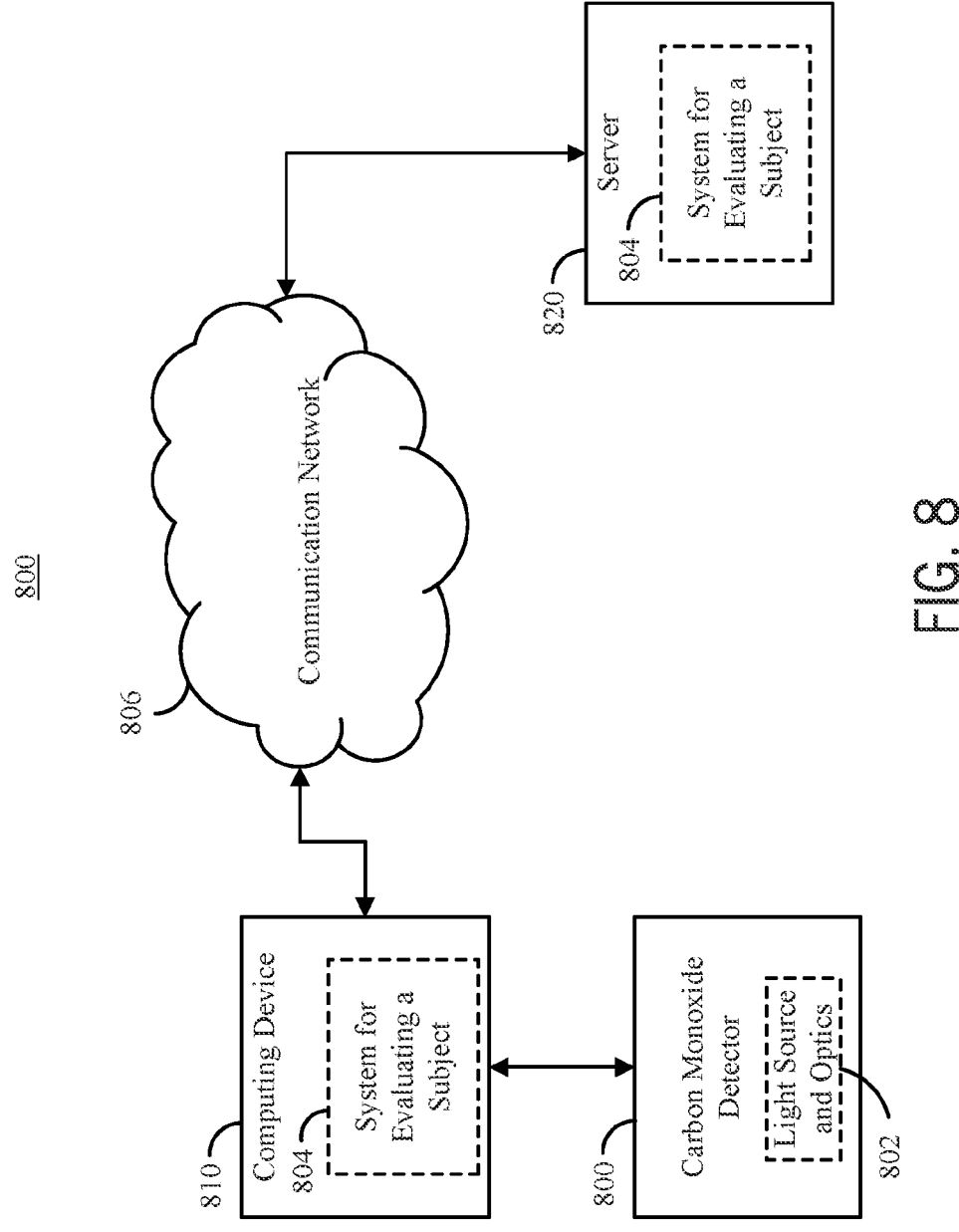
FIG. 8 shows an example of a system for evaluating a subject in accordance with some embodiments of the disclosed subject matter.

FIG. 8 shows an example 800 of a system (e.g., a data collection and processing system) for evaluating a subject is shown in accordance with some embodiments of the disclosed subject matter. As shown in FIG. 8, a computing device 810 can receive data pertaining to a measure of CO in a subject from a CO detector 800. In some embodiments, computing device 810 can execute at least a portion of a system for evaluating a subject 804 to obtain a level of at least one biomarker based on the CO measurement data received from the CO detector 800. Additionally or alternatively, in some embodiments, computing device 810 can communicate information about the CO measurement data received from the CO detector 800 to a server 820 over a communication network 806, which can execute at least a portion of system for evaluating a subject 804 to obtain a level of at least one biomarker based on the CO measurement data. In some such embodiments, server 820 can return information to computing device 810 (and/or any other suitable computing device) indicative of an output of system for evaluating a subject 804, such as a report based on obtaining the level of the at least one biomarker. This information may be transmitted and/or presented to a user (e.g., a researcher, an operator, a clinician, etc.) and/or may be stored (e.g., as part of a research database or a medical record associated with a subject).

In some embodiments, computing device 810 and/or server 820 can be any suitable computing device or combination of devices, such as a desktop computer, a laptop computer, a smartphone, a tablet computer, a wearable computer, a server computer, a virtual machine being executed by a physical computing device, etc. As described herein, system for evaluating a subject 804 can present information about the CO measurement and/or the report based on obtaining the level of the at least one biomarker to a user (e.g., researcher and/or physician).

In some embodiments, CO detector 800 may include a suitable light source and optics 802 for obtaining CO levels from the subject, e.g., through the skin. In other embodiments, light source and optics 802 can be local to computing device 810. For example, light source and optics 802 may be incorporated with computing device 810 (e.g., computing device 810 can be configured as part of a device for capturing and/or storing optical interferometric information). As another example, light source and optics 802 may be connected to computing device 810 by a cable, a direct wireless link, etc. Additionally or alternatively, in some embodiments, light source and optics 802 can be located locally and/or remotely from computing device 810, and can communicate information to computing device 810 (and/or server 820) via a communication network (e.g., communication network 806). In various embodiments, the light source and optics 802 may be disposed within a housing which includes the components of the CO detector 800 along with a processor, memory, and user interface.

In some embodiments, communication network 806 can be any suitable communication network or combination of communication networks. For example, communication network 806 can include a Wi-Fi network (which can include one or more wireless routers, one or more switches, etc.), a peer-to-peer network (e.g., a Bluetooth network), a cellular network (e.g., a 4G network, a 5G network, etc., complying with any suitable standard, such as CDMA, GSM, LTE, LTE Advanced, WiMAX, etc.), a wired network, etc. In some embodiments, communication network 806 can be a local area network, a wide area network, a public network (e.g., the Internet), a private or semi-private network (e.g., a corporate or university intranet), any other suitable type of network, or any suitable combination of networks. Communications links shown in FIG. 8 can each be any suitable communications link or combination of communications links, such as wired links, fiber optic links, Wi-Fi links, Bluetooth links, cellular links, etc.

Figure 9:
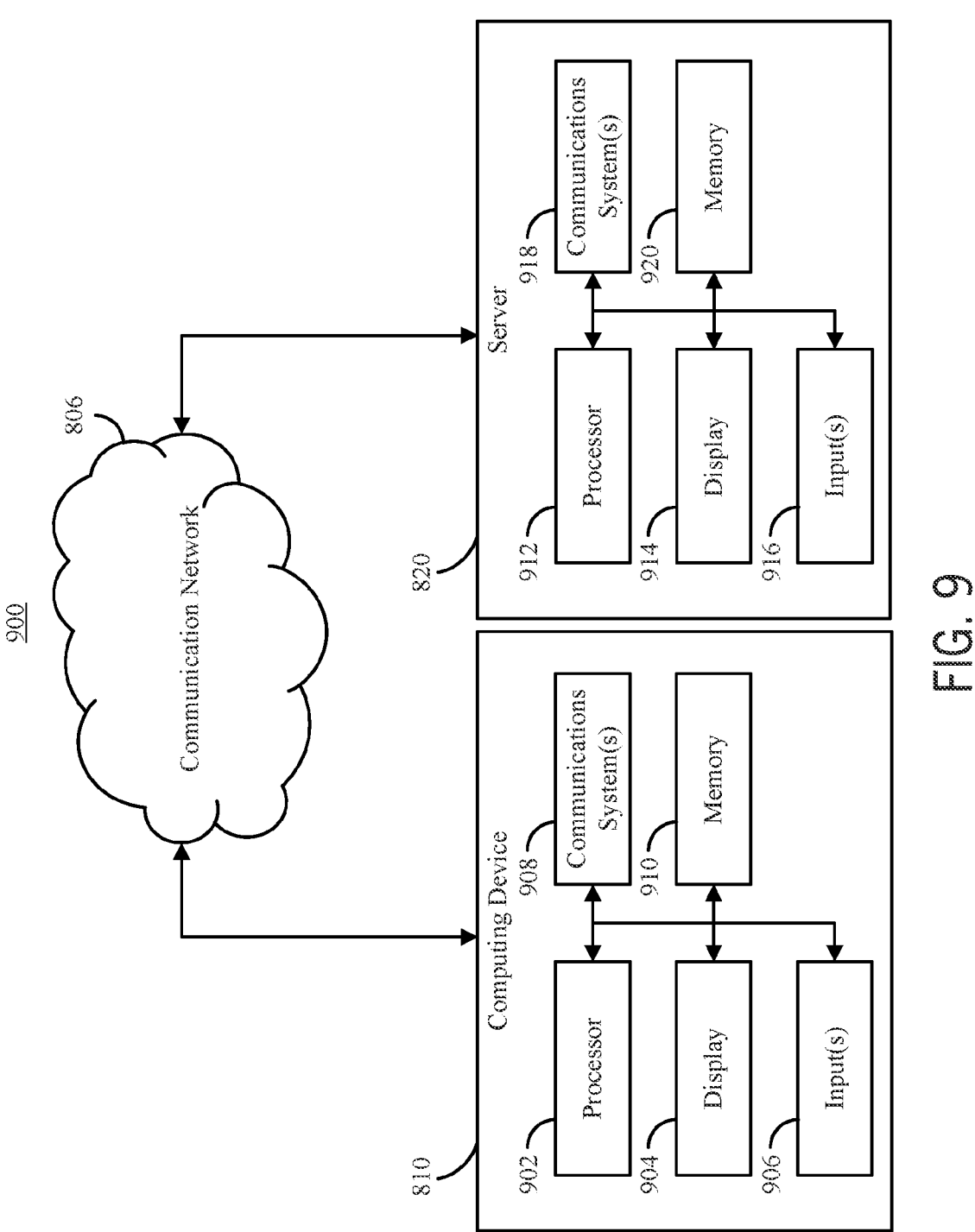
FIG. 9 shows an example of hardware that can be used to implement computing device and server in accordance with some embodiments of the disclosed subject matter.

FIG. 9 shows an example 900 of hardware that can be used to implement computing device 810 and server 820 in accordance with some embodiments of the disclosed subject matter. As shown in FIG. 9, in some embodiments, computing device 810 can include a processor 902, a display 904, one or more inputs 906, one or more communication systems 908, and/or memory 910. In some embodiments, processor 902 can be any suitable hardware processor or combination of processors, such as a central processing unit, a graphics processing unit, etc. In some embodiments, display 904 can include any suitable display devices, such as a computer monitor, a touchscreen, a television, etc. In some embodiments, inputs 906 can include any suitable input devices and/or sensors that can be used to receive user input, such as a keyboard, a mouse, a touchscreen, a microphone, etc.

In some embodiments, communications systems 908 can include any suitable hardware, firmware, and/or software for communicating information over communication network 806 and/or any other suitable communication networks. For example, communications systems 908 can include one or more transceivers, one or more communication chips and/or chip sets, etc. In a more particular example, communications systems 908 can include hardware, firmware and/or software that can be used to establish a Wi-Fi connection, a Bluetooth connection, a cellular connection, an Ethernet connection, etc.

In some embodiments, memory 910 can include any suitable storage device or devices that can be used to store instructions, values, etc., that can be used, for example, by processor 902 to present content using display 904, to communicate with server 820 via communications system(s) 908, etc. Memory 910 can include any suitable volatile memory, non-volatile memory, storage, or any suitable combination thereof. For example, memory 910 can include RAM, ROM, EEPROM, one or more flash drives, one or more hard disks, one or more solid state drives, one or more optical drives, etc. In some embodiments, memory 910 can have encoded thereon a computer program for controlling operation of computing device 810. In such embodiments, processor 902 can execute at least a portion of the computer program to present content (e.g., images, user interfaces, graphics, tables, etc.), receive content from server 820, transmit information to server 820, etc.

In some embodiments, server 820 can include a processor 912, a display 914, one or more inputs 916, one or more communications systems 918, and/or memory 920. In some embodiments, processor 912 can be any suitable hardware processor or combination of processors, such as a central processing unit, a graphics processing unit, etc. In some embodiments, display 914 can include any suitable display devices, such as a computer monitor, a touchscreen, a television, etc. In some embodiments, inputs 916 can include any suitable input devices and/or sensors that can be used to receive user input, such as a keyboard, a mouse, a touchscreen, a microphone, etc.

In some embodiments, communications systems 918 can include any suitable hardware, firmware, and/or software for communicating information over communication network 806 and/or any other suitable communication networks. For example, communications systems 918 can include one or more transceivers, one or more communication chips and/or chip sets, etc. In a more particular example, communications systems 918 can include hardware, firmware and/or software that can be used to establish a Wi-Fi connection, a Bluetooth connection, a cellular connection, an Ethernet connection, etc.

In some embodiments, memory 920 can include any suitable storage device or devices that can be used to store instructions, values, etc., that can be used, for example, by processor 912 to present content using display 914, to communicate with one or more computing devices 810, etc. Memory 920 can include any suitable volatile memory, non-volatile memory, storage, or any suitable combination thereof. For example, memory 920 can include RAM, ROM, EEPROM, one or more flash drives, one or more hard disks, one or more solid state drives, one or more optical drives, etc. In some embodiments, memory 920 can have encoded thereon a server program for controlling operation of server 820. In such embodiments, processor 912 can execute at least a portion of the server program to transmit information and/or content (e.g., results of a tissue identification and/or classification, a user interface, etc.) to one or more computing devices 810, receive information and/or content from one or more computing devices 810, receive instructions from one or more devices (e.g., a personal computer, a laptop computer, a tablet computer, a smartphone, etc.), etc.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as RAM, Flash memory, electrically programmable read only memory (EPROM), electrically erasable programmable read only memory (EE-PROM), etc.), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

In some embodiments, the optical signals are detected by photodiodes. It should be recognized that any opto-electronic conversion device including but not limited to photo detectors, photodiodes, line-scan and two-dimensional cameras, and photodiode arrays can be used to perform this detection function.

It should be noted that, as used herein, the term mechanism can encompass hardware, software, firmware, or any suitable combination thereof.

Figure 10:
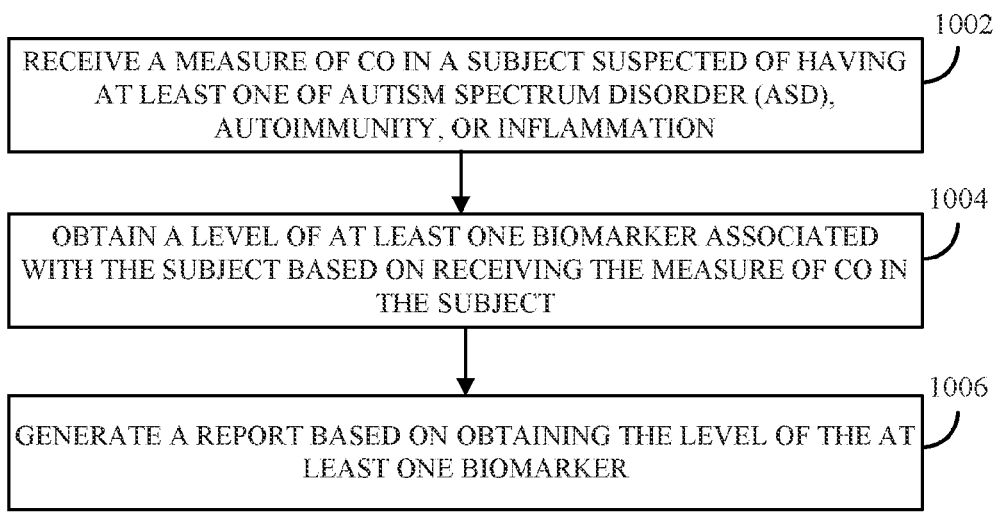
FIG. 10 shows an example of a process for evaluating a subject in accordance with some embodiments of the disclosed subject matter.

FIG. 10 shows an example 1000 of a process for evaluating a subject in accordance with some embodiments of the disclosed subject matter. As shown in FIG. 10, at 1002, process 1000 can receive a measure of CO in a subject suspected of having at least one of autism spectrum disorder (ASD), autoimmunity, or inflammation, where the measure of CO may be received from a CO detector in communication with a carbon monoxide (CO) detector. At 1004, process 1000 can obtain, by the processor, a level of at least one biomarker associated with the subject based on receiving the measure of CO in the subject. Finally, at 1006, process 1000 can generate, by the processor, a report based on obtaining the level of the at least one biomarker.

It should be understood that the above described steps of the process of FIG. 10 can be executed or performed in any order or sequence not limited to the order and sequence shown and described in the figures. Also, some of the above steps of the processes of FIG. 10 can be executed or performed substantially simultaneously where appropriate or in parallel to reduce latency and processing times.

FIG. 11 shows an example 1100 of a process for assessing efficacy of treatment of a subject suspected of having at least one of Autism Spectrum Disorder (ASD), autoimmunity, or inflammation in accordance with some embodiments of the disclosed subject matter. As shown in FIG. 11, at 1102, process 1100 can conduct a first evaluation of a subject suspected of having at least one of ASD, autoimmunity, or inflammation. At 1104, process 1100 can conduct a first evaluation by receiving, by a processor in communication with a carbon monoxide (CO) detector, a first measure of CO of the subject. At 1106, process 1100 can further conduct a first evaluation by obtaining, by the processor, a first level of at least one biomarker associated with the subject based on receiving the first measure of CO. At 1108, process 1100 can further conduct a first evaluation by generating, by the processor, a first report based on obtaining the first level of the at least one biomarker. At 1110, process 1100 can conduct a second evaluation of the subject following administration of a treatment to the subject. At 1112, process 1100 can conduct a second evaluation by receiving, by the processor from the CO detector, a second measure of CO of the subject. At 1114, process 1100 can further conduct a second evaluation by obtaining, by the processor, a second level of the at least one biomarker associated with the subject based on receiving the second measure of CO in the subject. At 1116, process 1100 can further conduct a second evaluation by generating, by the processor, a second report based on obtaining the second level of the at least one biomarker. Finally, at 1118, process 1100 can compare, by the processor, the first evaluation and the second evaluation.

It should be understood that the above described steps of the process of FIG. 11 can be executed or performed in any order or sequence not limited to the order and sequence shown and described in the figures. Also, some of the above steps of the processes of FIG. 11 can be executed or performed substantially simultaneously where appropriate or in parallel to reduce latency and processing times.

REFERENCES

1. Maenner M J, Shaw K A, Baio J, EdS1, Washington A, Patrick M, et al. Prevalence of Autism Spectrum Disorder Among Children Aged 8 Years—Autism and Developmental Disabilities Monitoring Network, 11 Sites, United States, 2016. Mmwr Surveill Summ. 2020; 69:1-12.
2. Alam R, Abdolmaleky H M, Zhou J. Microbiome, inflammation, epigenetic alterations, and mental diseases. Am J Medical Genetics Part B Neuropsychiatric Genetics. 2017; 174:651-60.
3. Braunschweig D, Krakowiak P, Duncanson P, Boyce R, Hansen R L, Ashwood P, et al. Autism-specific maternal autoantibodies recognize critical proteins in developing brain. Transl Psychiat. 2013; 3: e277.
4. Cao X, Liu K, Liu J, Liu Y-W, Xu L, Wang H, et al. Dysbiotic Gut Microbiota and Dysregulation of Cytokine Profile in Children and Teens With Autism Spectrum Disorder. Front Neurosci-switz. 2021; 15:635925.
5. Connery K, Tippett M, Delhey L M, Rose S, Slattery J C, Kahler S G, et al. Intravenous immunoglobulin for the treatment of autoimmune encephalopathy in children with autism. Transl Psychiat. 2018; 8:148.
6. Kong X-J, Liu J, Liu K, Koh M, Sherman H, Liu S, et al. Probiotic and Oxytocin Combination Therapy in Patients with Autism Spectrum Disorder: A Randomized, Double-Blinded, Placebo-Controlled Pilot Trial. Nutrients. 2021; 13:1552.
7. Melamed I R, Heffron M, Testori A, Lipe K. A pilot study of high-dose intravenous immunoglobulin 5% for autism: Impact on autism spectrum and markers of neuroinflammation. Autism Res. 2018; 11:421-33.
8. Guloksuz S A, Abali O, Cetin E A, Gazioglu S B, Deniz G, Yildirim A, et al. Elevated plasma concentrations of S100 calcium-binding protein B and tumor necrosis factor alpha in children with autism spectrum disorders. Rev Bras Psiquiatr. 2017; 39:195-200.
9. Masi A, *Quintana* D S, Glozier N, Lloyd A R, Hickie I B, Guastella A J. Cytokine aberrations in autism spectrum disorder: a systematic review and meta-analysis. Mol Psychiatr. 2015; 20:440-6.
10. Esnafoglu E, Ayy$_1$ld$_{1z}$ S N, C1rr1k S, Erturk E Y, Erdil A, Dagl$_1$ A, et al. Evaluation of serum Neuron-specific enolase, S100B, myelin basic protein and glial fibrilliary acidic protein as brain specific proteins in children with autism spectrum disorder. Int J Dev Neurosci. 2017; 61:86-91.
11. Abou-Donia M B, Suliman H B, Siniscalco D, Antonucci N, ElKafrawy P, Brahmajothi M V. de novo Blood Biomarkers in Autism: Autoantibodies against Neuronal and Glial Proteins. Behav Sci. 2019; 9:47.
12. Gonzalez-Gronow M, Cuchacovich M, Francos R, Cuchacovich S, Blanco A, Sandoval R, et al. Catalytic autoantibodies against myelin basic protein (MBP) isolated from serum of autistic children impair in vitro models of synaptic plasticity in rat hippocampus. J Neuroimmunol. 2015; 287:1-8.
13. Kern J K, Geier D A, Sykes L K, Geier M R. Relevance of Neuroinflammation and Encephalitis in Autism. Front Cell Neurosci. 2016; 9:519.
14. Mostafa G A, A L-Ayadhi L Y. A lack of association between hyperserotonemia and the increased frequency of serum anti-myelin basic protein auto-antibodies in autistic children. J Neuroinflamm. 2011; 8:71-71.
15. Kealy J, Greene C, Campbell M. Blood-brain barrier regulation in psychiatric disorders. Neurosci Lett. 2018; 726:133664.
16. Zou T, Liu J, Zhang X, Tang H, Song Y, Kong X. Autoantibody and autism spectrum disorder: A systematic review. Res Autism Spect Dis. 2020; 75:101568.
17. Connolly A M, Chez M, Streif E M, Keeling R M, Golumbek P T, Kwon J M, et al. Brain-Derived Neurotrophic Factor and Autoantibodies to Neural Antigens in Sera of Children with Autistic Spectrum Disorders, Landau-Kleffner Syndrome, and Epilepsy. Biol Psychiat. 2006; 59:354-63.
18. Connolly A M, Chez M G, Pestronk A, Arnold S T, Mehta S, Deuel R K. Serum autoantibodies to brain in Landau-Kleffner variant, autism, and other neurologic disorders. J Pediatrics. 1999; 134:607-13.
19. Bashir S, Al-Ayadhi L. Endothelial antibody levels in the sera of children with autism spectrum disorders. J Chin Med Assoc. 2015; 78:414-7.
20. Sakurai Y. Autoimmune Aspects of Kawasaki Disease. J Invest Allerg Clin. 2019; 29:251-61.
21. Paval D. A Dopamine Hypothesis of Autism Spectrum Disorder. Dev Neurosci-basel. 2017; 39:355-60.
22. Cox C J, Zuccolo A J, Edwards E V, Mascaro-Blanco A, Alvarez K, Stoner J, et al. Antineuronal Antibodies in a Heterogeneous Group of Youth and Young Adults with Tics and Obsessive-Compulsive Disorder. J Child Adol Psychop. 2015; 25:76-85.
23. Kirvan C A, Swedo S E, Snider L A, Cunningham M W. Antibody-mediated neuronal cell signaling in behavior and movement disorders. J Neuroimmunol. 2006; 179:173-9.
24. Morita M, Wang Y, Sasaoka T, Okada K, Niwa M, Sawa A, et al. Dopamine D2L Receptor Is Required for Visual Discrimination and Reversal Learning. Mol Neuropsychiatry. 2016; 2:124-32.
25. Breuss M W, Leca I, Gstrein T, Hansen A H, Keays D A. Tubulins and brain development-The origins of functional specification. Mol Cell Neurosci. 2017; 84:58-67.
26. Dale R C, Merheb V, Pillai S, Wang D, Cantrill L, Murphy T K, et al. Antibodies to surface dopamine-2 receptor in autoimmune movement and psychiatric disorders. Brain. 2012; 135:3453-68.

27. Yang X, Liang S, Wang L, Han P, Jiang X, Wang J, et al. Sialic acid and anti-ganglioside antibody levels in children with autism spectrum disorders. Brain Res. 2018; 1678:273-7.

28. Ryter S W. Heme oxygenase-1/carbon monoxide as modulators of autophagy and inflammation. Arch Biochem Biophys. 2019; 678:108186.

29. Ryter S W, Choi AMK. Targeting heme oxygenase-1 and carbon monoxide for therapeutic modulation of inflammation. Transl Res. 2016; 167:7-34.

30. Kwong K K, Chan S. The role of carbon monoxide and heme oxygenase-1 in COVID-19. Toxicol Reports. 2020; 7:1170-1.

31. Wagener FADTG, Pickkers P, Peterson S J, Immenschuh S, Abraham N G. Targeting the Heme-Heme Oxygenase System to Prevent Severe Complications Following COVID-19 Infections. Antioxidants. 2020; 9:540.

32. Kong X, Liu J, Cetinbas M, Sadreyev R, Koh M, Huang H, et al. New and Preliminary Evidence on Altered Oral and Gut Microbiota in Individuals with Autism Spectrum Disorder (ASD): Implications for ASD Diagnosis and Subtyping Based on Microbial Biomarkers. Nutrients. 2019; 11:2128.

33. Kong X-J, Liu J, Li J, Kwong K, Koh M, Sukijthamapan P, et al. Probiotics and oxytocin nasal spray as neuro-social-behavioral interventions for patients with autism spectrum disorders: a pilot randomized controlled trial protocol. Pilot Feasibility Stud. 2020; 6:20.

34. Fattorusso A, Genova L D, Dell'Isola G B, Mencaroni E, Esposito S. Autism Spectrum Disorders and the Gut Microbiota. Nutrients. 2019; 11:521.

35. Liu Y-W, Liong M T, Chung Y-C E, Huang H-Y, Peng W-S, Cheng Y-F, et al. Effects of *Lactobacillus plantarum* PS128 on Children with Autism Spectrum Disorder in Taiwan: A Randomized, Double-Blind, Placebo-Controlled Trial. Nutrients. 2019; 11:820.

36. Liu W-H, Yang C-H, Lin C-T, Li S-W, Cheng W-S, Jiang Y-P, et al. Genome architecture of *Lactobacillus plantarum* PS128, a probiotic strain with potential immunomodulatory activity. Gut Pathog. 2015; 7:22.

37. Erdman S E, Poutahidis T. Chapter Five Microbes and Oxytocin Benefits for Host Physiology and Behavior. Int Rev Neurobiol. 2016; 131:91-126.

38. MATSUURA T, MOTOJIMA Y, KAWASAKI M, OHNISHI H, SAKAI A, UETA Y. [Relationship Between Oxytocin and Pain Modulation and Inflammation]. J Uoeh. 2016; 38:325-34.

39. Light A, Grass C, Pursley D, Krause J. Carboxyhemoglobin levels in smokers vs. non-smokers in a smoking environment. Respir Care. 2007; 52.

40. Schimmel J, George N, Schwarz J, Yousif S, Suner S, Hack J B. Carboxyhemoglobin Levels Induced by Cigarette Smoking Outdoors in Smokers. J Medical Toxicol. 2018; 14:68-73.

41. Shimasaki C, Frye R E, Trifiletti R, Cooperstock M, Kaplan G, Melamed I, et al. Evaluation of the Cunningham PanelTM in pediatric autoimmune neuropsychiatric disorder associated with streptococcal infection (PANDAS) and pediatric acute-onset neuropsychiatric syndrome (PANS): Changes in antineuronal antibody titers parallel changes in patient symptoms. J Neuroimmunol. 2020; 339:577138.

42. Chain J L, Alvarez K, Mascaro-Blanco A, Reim S, Bentley R, Hommer R, et al. Autoantibody Biomarkers for Basal Ganglia Encephalitis in Sydenham Chorea and Pediatric Autoimmune Neuropsychiatric Disorder Associated With Streptococcal Infections. Frontiers Psychiatry. 2020; 11:564.

43. Lewis S J, Heaton K W. Stool Form Scale as a Useful Guide to Intestinal Transit Time. Scand J Gastroentero. 2009; 32:920-4.

44. Bölte S, Poustka F, Constantino J N. Assessing autistic traits: cross-cultural validation of the social responsiveness scale (SRS). Autism Res. 2008; 1:354-63.

45. Aman M G, Singh N N, Stewart A W, Field C J. The aberrant behavior checklist: a behavior rating scale for the assessment of treatment effects. Am J Ment Defic. 1985; 5:485-91.

46. Busner J, Targum S D. The clinical global impressions scale: applying a research tool in clinical practice. Psychiatry (Edgmont). 2007; 28-37.

47. McIver L J, Abu-Ali G, Franzosa E A, Schwager R, Morgan X C, Waldron L, et al. bioBakery: a meta'omic analysis environment. Bioinformatics. 2018; 34:1235-7.

48. DeSantis T Z, Hugenholtz P, Larsen N, Rojas M, Brodie E L, Keller K, et al. Greengenes, a Chimera-Checked 16S rRNA Gene Database and Workbench Compatible with ARB. Appl Environ Microb. 2006; 72:5069-72.

49. Segata N, Izard J, Waldron L, Gevers D, Miropolsky L, Garrett W S, et al. Metagenomic biomarker discovery and explanation. Genome Biol. 2011; 12: R60-R60.

50. DiStasio M M, Nagakura I, Nadler M J, Anderson M P. T lymphocytes and cytotoxic astrocyte blebs correlate across autism brains. Ann Neurol. 2019; 86:885-98.

51. Liu H, Wang J, He T, Becker S, Zhang G, Li D, et al. Butyrate: A Double-Edged Sword for Health? Adv Nutr. 2018; 9:21-9.

52. Strati F, Cavalieri D, Albanese D, Felice C D, Donati C, Hayek J, et al. New evidences on the altered gut microbiota in autism spectrum disorders. Microbiome. 2017; 5:24.

53. Weisman O, Feldman R. Oxytocin administration affects the production of multiple hormones. Psychoneuroendocrino. 2013; 38:626-7.

Thus, while the invention has been described above in connection with particular embodiments and examples, the invention is not necessarily so limited, and that numerous other embodiments, examples, uses, modifications and departures from the embodiments, examples and uses are intended to be encompassed by the claims attached hereto.

What is claimed is:

1. A system for evaluating a subject, comprising:
a housing,
a processor in communication with a carbon monoxide (CO) detector, and
a memory in communication with the processor having stored thereon a set of instructions which, when executed by the processor, cause the processor to:
receive, from the CO detector, a measure of CO in a subject suspected of having at least one of autism spectrum disorder (ASD), autoimmunity, or inflammation;
determine a measure of ASD severity associated with the subject based on receiving the measure of CO in the subject by comparing the measure of CO to a calibration curve correlating the measure of ASD severity to the measure of CO; and

report the correlation between the measure of ASD
severity to the measure of CO,
wherein the CO detector, the processor, and the
memory are disposed within the housing.
2. The system of claim 1, wherein the processor, when
receiving a measure of CO in a subject, is further caused by
the instructions to:
receive a level of blood carbon monoxide (SpCO) in the
subject.
3. The system of claim 1, wherein the system further
comprises a user interface,
wherein the user interface is disposed within the housing,
and
wherein the housing is configured to be coupled to the
subject.
4. The system of claim 1, wherein the measure of CO
comprises an average of measurements collected at a first
time point and a second time point.
5. The system of claim 1, wherein the processor, when
generating the report, is further caused by the instructions to:
generate the report indicating a level of ganglioside-
monosialic acid (GM1) in the subject.
6. The system of claim 1, wherein the processor, when
generating the report, is further caused by the instructions to:
generate the report indicating a treatment for the subject
suspected of having at least one of ASD, autoimmunity,
or inflammation.
7. The system of claim 6, wherein the processor, when
indicating the treatment for the subject suspected of having
at least one of ASD, autoimmunity, or inflammation, is
further caused by the instructions to:
indicate the treatment comprising administration of a
probiotic to the subject suspected of having at least one
of ASD, autoimmunity, or inflammation.
8. The system of claim 7, wherein the processor, when
indicating the treatment comprising administration of a
probiotic to the subject suspected of having at least one of
ASD, autoimmunity, or inflammation, is further caused by
the instructions to:
indicate the treatment comprising administration of *Lac-
tobacillus plantarum* probiotic to the subject suspected
of having at least one of ASD, autoimmunity, or inflam-
mation.
9. The system of claim 6, wherein the treatment is
administered to the subject suspected of having at least one
of ASD, autoimmunity, or inflammation for at least 16
weeks.
10. The system of claim 1, wherein the processor, when
generating the report, is further caused by the instructions to:
generate the report indicating a subgrouping of the subject
suspected of having ASD.
11. The system of claim 1, wherein the processor is further
caused by the instructions to:
obtain a level of at least one biomarker based on a
correlation between the measure of CO and level of the
at least one biomarker.
12. A method for evaluating a subject, comprising:
providing a housing;
receiving, from a processor in communication with a
carbon monoxide (CO) detector, a measure of CO in a subject suspected of having at least one of autism
spectrum disorder (ASD), autoimmunity, or inflamma-
tion,
wherein the processor and the CO detector are disposed
within the housing;
determining, by the processor, a measure of ASD severity
associated with the subject based on receiving the
measure of CO in the subject by comparing the mea-
sure of CO to a calibration curve correlating the mea-
sure of ASD severity to the measure of CO; and
reporting the correlation between the measure of ASD
severity to the measure of CO.
13. The method of claim 12, wherein receiving the
measure of CO in the subject further comprises:
receiving a level of blood carbon monoxide (SpCO) in the
subject.
14. The method of claim 12, wherein a user interface is
disposed within the housing, and
wherein the housing is configured to be coupled to the
subject.
15. The method of claim 12, wherein the measure of CO
comprises an average of measurements collected at a first
time point and a second time point.
16. The method of claim 12, wherein generating the report
further comprises:
generating the report indicating a level of ganglioside-
monosialic acid (GM1) in the subject.
17. The method of claim 12, wherein generating the report
further comprises:
generating the report indicating a treatment for the subject
suspected of having at least one of ASD, autoimmunity,
or inflammation.
18. The method of claim 17, wherein indicating the
treatment for the subject suspected of having at least one of
ASD, autoimmunity, or inflammation further comprises:
indicating the treatment comprising administration of a
probiotic to the subject suspected of having at least one
of ASD, autoimmunity, or inflammation.
19. The method of claim 18, wherein indicating the
treatment comprising administration of the probiotic to the
subject suspected of having at least one of ASD, autoim-
munity, or inflammation further comprises:
indicating the treatment comprising administration of
*Lactobacillus plantarum* probiotic to the subject sus-
pected of having at least one of ASD, autoimmunity, or
inflammation.
20. The method of claim 17, wherein the treatment is
administered to the subject suspected of having at least one
of ASD, autoimmunity, or inflammation for at least 16
weeks.
21. The method of claim 12, wherein generating the report
further comprises:
generating the report indicating a subgrouping of the
subject suspected of having ASD.
22. The method of claim 12, wherein the method further
comprises:
obtaining a level of at least one biomarker based on a
correlation between the measure of CO and the level of
the at least one biomarker.

* * * * *